(12) United States Patent
Costantino et al.

(10) Patent No.: US 11,065,323 B2
(45) Date of Patent: Jul. 20, 2021

(54) PURIFICATION METHOD

(75) Inventors: Paolo Costantino, Siena (IT);
Francesco Berti, Siena (IT); Anna Kabanova, Siena (IT); Maria Rosaria Romano, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 13/126,146

(22) PCT Filed: Oct. 27, 2009

(86) PCT No.: PCT/IB2009/007346
§ 371 (c)(1),
(2), (4) Date: Sep. 29, 2011

(87) PCT Pub. No.: WO2010/049806
PCT Pub. Date: May 6, 2010

(65) Prior Publication Data
US 2012/0010398 A1    Jan. 12, 2012

Related U.S. Application Data

(60) Provisional application No. 61/108,763, filed on Oct. 27, 2008.

(51) Int. Cl.
| | |
|---|---|
| C07H 5/06 | (2006.01) |
| A61K 39/09 | (2006.01) |
| B01D 15/34 | (2006.01) |
| B01D 15/36 | (2006.01) |
| B01D 61/14 | (2006.01) |
| A61K 39/00 | (2006.01) |

(52) U.S. Cl.
CPC ............ *A61K 39/092* (2013.01); *B01D 15/34* (2013.01); *B01D 15/363* (2013.01); *A61K 2039/55505* (2013.01); *A61K 2039/6037* (2013.01); *B01D 61/145* (2013.01)

(58) Field of Classification Search
CPC ........ A61K 39/092; A61K 2039/55505; A61K 2039/6037; B01D 15/34; B01D 15/363; B01D 61/145
USPC .......................... 536/127, 123.1, 123; 514/54
See application file for complete search history.

(56) References Cited

U.S. PATENT DOCUMENTS

| | | | | |
|---|---|---|---|---|
| 5,001,112 A | * | 3/1991 | Hofstead | C07K 14/36 435/71.3 |
| 5,252,457 A | * | 10/1993 | Snodgrass | C07C 243/38 435/184 |
| 5,837,520 A | * | 11/1998 | Shabram | C08F 265/02 435/239 |
| 5,866,135 A | | 2/1999 | Blake et al. | |
| 6,548,287 B1 | * | 4/2003 | Powell et al. | 435/243 |
| 7,332,173 B2 | | 2/2008 | Blake et al. | |

FOREIGN PATENT DOCUMENTS

| | | | |
|---|---|---|---|
| EP | 1801217 A1 | 6/2007 | |
| JP | 0346467 A1 * | 12/1989 | ......... C08B 37/0072 |
| WO | WO-87/06267 | 10/1987 | |
| WO | 2007/084856 A2 | 7/2007 | |
| WO | WO-2008/118752 | 10/2008 | |

OTHER PUBLICATIONS

Savel'ev et al. (Prikladnaia biokhimiia i mikrobiologiia, (Jan.-Feb. 1978) vol. 14, No. 1, pp. 38-43) (Abstract Sent).*
Cunningham (Clinical Microbiology Reviews, Jul. 2000, vol. 13, No. 3, p. 470-511).*
Cunningham et al. (Infection and Immunity, Sep. 1976, p. 767-775).*
Degnan et al. (Infection and Immunity, Jul. 1998, p. 3050-3058).*
Fischetti (BMC Oral Health 2006, 6(Suppl 1):S16, pp. 1-4).*
Van De Rijn (Journal of Bacteriology, Dec. 1983, p. 1059-1065).*
Bisno et al. (2005). "Prospects for a group a streptococcal vaccine: rationale, feasibility, and obstacles—report of a National Institute of Allergy and Infectious Diseases workshop," Clin Infect Dis. 41(8):1150-6. Epub Sep. 2, 2005.
Borrelli et al. (2006). "Immunological Evidence for Peptide-Carbohydrate Mimicry with a Group A *Streptococcus* Polysaccharide-Mimetic Peptide," American Journal of Immunology 2(4):77-87.
Cohen-Poradosu et al. (2007). "Group A *streptococcus* epidemiology and vaccine implications," Clin Infect Dis. 45(7):863-5. Epub Aug. 29, 2007.
DuBois et al. (1956). "Colorimetric Method for Determination of Sugars and Related Substances," Anal. Chem., 1956, 28 (3), pp. 350-356.
McCarty. (1958). "Further studies on the chemical basis for serological specificity of Group A streptococcal carbohydrate," J Exp Med.108(3):311-23.
Michon et al. (2005). "Doubly branched hexasaccharide epitope on the cell wall polysaccharide of group A streptococci recognized by human and rabbit antisera," Infect Immun. 73(10):6383-9.
Pancholi et al. (1988). "Isolation and characterization of the cell-associated region of group A streptococcal M6 protein," J Bacteriol. 170(6): 2618-2624.
Sabharwal et al. (2006). "The streptococcal group A carbohydrate protects against nasal colonization with group A streptococci in mice," International Congress Series, vol. 1289, pp. 329-331.

(Continued)

*Primary Examiner* — Shaojia A Jiang
*Assistant Examiner* — Michael C Henry
(74) *Attorney, Agent, or Firm* — Birch, Stewart, Kolasch & Birch, LLP

(57) ABSTRACT

A process for purifying a *Streptococcus pyogenes* GAS carbohydrate comprising a step of anionic exchange chromatography. The process provides a good yield of GAS carbohydrate. The saccharides of the invention have low levels of hyaluronic acid, protein and nucleic acid contamination.

21 Claims, 15 Drawing Sheets

(56) References Cited

OTHER PUBLICATIONS

World Health Organization, Department of Child and Adolescent Health and Development (2005). "Group A streptococcal vaccine development: current status and issues of relevance to less developed countries." 24 pages.
Costantino et al. (Mar. 5, 1999) "Size fractionation of bacterial capsular polysaccharides for their use in conjugate vaccines," Vaccine 17(9-10):1251-1263.
Sabharwal et al. (Jan. 1, 2006) "Group A *streptococcus* (GAS) carbohydrate as an immunogen for protection against GAS infection," The Journal of Infectious Diseases 193(1):129-135.
International Search Report and Written Opinion dated Mar. 18, 2010, for PCT/IB2009/007346 filed Oct. 27, 2008, 14 pages.
Office Action received for Japanese Patent Application No. 2011-532737, dated Dec. 26, 2013, 7 pages (4 pages of English Translation and 3 pages of JPOA).
Pato et al., "Purification of Capsular Polysaccharide from Neisseria Meningitidis Serogroup C by Liquid Chromatography", Journal of Chromatography B, vol. 832, 2006, pp. 262-267.

\* cited by examiner

Enlargement of 5,4-3,4 ppm region:

1)

2)

PURIFICATION METHOD

CROSS REFERENCE TO RELATED APPLICATIONS

This application is a U.S. National Phase patent application of PCT/IB2009/007346, filed Oct. 27, 2009, which claims priority to U.S. Provisional Application Ser. No. 61/108,763, filed on Oct. 27, 2008, all of which are incorporated by reference herein in their entirety.

TECHNICAL FIELD

This invention is in the field of purifying bacterial polysaccharides, particularly those of *Streptococcus pyogenes*, and particularly for use in the preparation of vaccines.

BACKGROUND ART

Polysaccharides from bacteria have been used for many years in vaccines. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 95].

Another bacterium for which conjugate vaccines have been described is *Streptococcus pyogenes*, also known as 'group A *streptococcus*', or simply as 'GAS'. The conjugate vaccines comprise the GAS carbohydrate, which is a component of the bacterial cell wall. Much of this work has been performed by John Zabriskie and colleagues, and is discussed in documents such as refs. 1, 2 and 3.

The starting point for saccharide-based vaccines is the saccharide itself, and this is generally purified from the target bacterium. The Zabriskie process for purification of the GAS carbohydrate is based on the methods of refs. 4 and 5 and is described in detail in ref. 6. Another method used by Zabriskie is based on the similar method of ref. 7, as described in ref. 8 and 9. Another method is described in ref. 10. These methods involve the extraction of GAS carbohydrate by reductive acid treatment. Specifically, *Streptococcus pyogenes* cells are combined with sodium nitrite and glacial acetic acid in order to lyse the cells and thereby release GAS carbohydrate. The resultant cell lysate suspension is then purified by size exclusion chromatography (as in ref. 10), for example by gel filtration using phosphate-buffered saline as eluant (as in ref. 6), or else clarified by tangential flow filtration (as in ref. 8), prior to conjugation of the GAS carbohydrate with a suitable carrier protein.

Refs. 6 and 8-10 do not indicate what yield of GAS carbohydrate is achieved by the purification methods used. Moreover, although refs. 6 and 8 state that the resultant GAS carbohydrate preparations "contain less than 1% (w/w) proteins and nucleic acids" [6] or are "free of proteins and nucleic acids" [8], there is no suggestion to remove impurities other than proteins or nucleic acids. There is thus a need for further and improved processes for purifying GAS carbohydrate, and particularly for processes that achieve higher yields and purities.

DISCLOSURE OF THE INVENTION

The invention is based on a purification process in which the saccharide is subjected to anionic exchange chromatography. The inventors have found that anionic exchange chromatography provides a good yield of GAS carbohydrate. Moreover, anionic exchange chromatography provides a particularly pure GAS carbohydrate preparation. In particular, the inventors have discovered that GAS carbohydrate is often contaminated with hyaluronic acid, which is derived from the GAS capsular polysaccharide. Anionic exchange chromatography is particularly effective at reducing hyaluronic acid contamination of GAS carbohydrate. This is particularly advantageous when the GAS carbohydrate is intended for use in a vaccine because hyaluronic acid is known to be immunogenic in its own right [11]. Accordingly, the presence of hyaluronic acid may interfere with the immune response to the GAS carbohydrate. Moreover, hyaluronic acid is thought to induce antibodies that are cross-reactive with human tissue ([12] and [13]), so its presence in pharmaceutical products may be detrimental to health. Anionic exchange chromatography is also particularly effective at reducing protein and nucleic acid contamination of GAS carbohydrate.

As a further advantage, the inventors have found that purification of GAS carbohydrate can be performed under conditions that allow "flow through" of the saccharide during anionic exchange chromatography, wherein impurities bind to the anion exchange matrix while GAS carbohydrate flows straight through the system into the eluant. The use of these conditions simplifies the purification process, as there is no need to use a mobile phase buffer of increasing ionic strength or increasing pH etc. to elute the GAS carbohydrate from the matrix.

The inventors have also discovered that GAS carbohydrate is often contaminated with a polyrhamnosyl variant of the GAS carbohydrate. The purification process of the present invention is particularly effective at reducing polyrhamnose contamination of GAS carbohydrate.

Accordingly, the invention provides a process for purifying a *Streptococcus pyogenes* GAS carbohydrate comprising a step of anionic exchange chromatography. The *Streptococcus pyogenes* GAS carbohydrate may be comprised within a suspension comprising at least one of hyaluronic acid, streptococcal proteins and nucleic acids. In particular, the invention provides a process for separating GAS carbohydrate from hyaluronic acid, comprising a step of anionic exchange chromatography. The hyaluronic acid will typically be derived from the *Streptococcus pyogenes* capsular polysaccharide. Other purification steps may be included in the process, either before or after the step of anionic exchange chromatography. For example, filtration step(s) can be included to remove high molecular weight contaminants (such as cellular debris). Similarly, ultrafiltration step(s) can be included, particularly after said filtration step(s), to remove low molecular weight contaminants (such as fragments of *Streptococcus pyogenes* polysaccharides). Gel filtration step(s) can also be included to select GAS carbohydrate molecules of a particular length and to reduce contamination, particularly by proteins. In addition to, or instead of, gel filtration step(s), the process of the invention may involve one or more steps of concentrating the GAS carbohydrate. Filtration and/or ultrafiltration step(s) will typically be performed before the anionic exchange chromatography step, while gel filtration step(s) and/or concentration step(s) will typically be performed after that step. The GAS carbohydrate saccharide can be processed for subsequent vaccine preparation. Various processing steps may therefore be included in the process, such as dialysis and/or lyophilisation steps. The process may also include a step of conjugating the purified GAS carbohydrate to a carrier molecule. Typically, the conjugation step is performed after the above purification step(s).

Accordingly, the invention provides, in a process for purifying the *Streptococcus pyogenes* GAS carbohydrate, the improvement consisting of the use of anionic exchange chromatography. The anionic exchange chromatography results in a good yield of GAS carbohydrate with limited hyaluronic acid, protein and nucleic acid contamination.

The yield of the anionic exchange chromatography step is typically greater than 70% (e.g. >75%, >80%, >85%, >90%). Practical limitations mean that the yield might not exceed 90% (e.g. might be ≤90%, ≤80%, ≤75%, etc.).

The invention also provides a process for purifying GAS carbohydrate from *Streptococcus pyogenes* bacteria, wherein the process provides a composition comprising a level of hyaluronic acid contamination that is less than 200 ng/ml (e.g. ≤150 ng/ml, ≤100 ng/ml, ≤90 ng/ml, ≤80 ng/ml, ≤75 ng/ml, ≤60 ng/ml, ≤50 ng/ml, ≤40 ng/ml, ≤25 ng/ml, ≤20 ng/ml, ≤10 ng/ml etc.). Typically, the level of hyaluronic acid contamination is less than 100 ng/ml, particularly less than 80 ng/ml. The level of hyaluronic acid contamination may also be expressed in terms of the weight of hyaluronic acid relative to the weight of GAS carbohydrate that is present in the purified sample. In this way, the invention provides a process for purifying GAS carbohydrate from *Streptococcus pyogenes* bacteria, wherein the process provides a composition comprising a level of hyaluronic acid contamination that is less than 5% (e.g. ≤4%, ≤3%, ≤2%, ≤1%, ≤0.75%, ≤0.5%, ≤0.25%, ≤0.1% etc.) by weight of hyaluronic acid relative to the weight of GAS carbohydrate. Typically, the level of hyaluronic acid contamination is less than 1% by weight of hyaluronic acid relative to the weight of GAS carbohydrate. Levels lower than this, e.g. equal to or less than 0.005% by weight of hyaluronic acid relative to the weight of GAS carbohydrate are also obtainable.

The invention also provides a process for purifying GAS carbohydrate from *Streptococcus pyogenes* bacteria, wherein the process provides a composition comprising a level of polyrhamnose contamination that is less than 50% (e.g. ≤40%, ≤30%, ≤25%, ≤20%, ≤15%, ≤10%, ≤8%, ≤6%, ≤5%, ≤4%, ≤2%, ≤1% etc.) by weight of polyrhamnose relative to the weight of GAS carbohydrate. Typically, the level of polyrhamnose contamination is less than 20% by weight of polyrhamnose relative to the weight of GAS carbohydrate. Levels lower than this, e.g. equal to or less than 5% by weight of polyrhamnose relative to the weight of GAS carbohydrate are also obtainable.

The invention also provides a process for purifying GAS carbohydrate from *Streptococcus pyogenes* bacteria, wherein the process provides a composition comprising a level of protein contamination that is less than 4.0% (e.g. ≤3.5%, ≤3.1%, ≤3.0%, ≤2.5%, ≤2.0%, ≤1.5%, ≤1.0%, etc.) by weight of protein relative to the weight of GAS carbohydrate. Typically, the level of protein contamination is around 2% by weight of protein relative to the weight of GAS carbohydrate.

The invention also provides a process for purifying GAS carbohydrate from *Streptococcus pyogenes* bacteria, wherein the process provides a composition comprising a level of nucleic acid contamination that is less than 5% (e.g. ≤4%, ≤3%, ≤2%, ≤1%, ≤0.75%, ≤0.5%, ≤0.25%, ≤0.1% etc.) by weight of nucleic acid relative to the weight of GAS carbohydrate. Typically, the level of nucleic acid contamination is less than 1% by weight of nucleic acid relative to the weight of GAS carbohydrate. Levels lower than this, e.g. less than 0.5% by weight of nucleic acid relative to the weight of GAS carbohydrate are also obtainable.

The invention also provides a process for purifying GAS carbohydrate from *Streptococcus pyogenes* bacteria, wherein (a) the level of hyaluronic acid contamination is less than 200 ng/ml or 5% (as described above); (b) the level of polyrhamnose contamination is less than 50% (as described above); (c) the level of protein contamination is less than 4.0% (as described above), and (d) the level of nucleic acid contamination that is less than 5% (as described above).

The invention also provides a composition comprising GAS carbohydrate from *Streptococcus pyogenes*, obtainable by the processes of the invention.

The invention also provides a composition comprising GAS carbohydrate from *Streptococcus pyogenes*, wherein the composition comprises a level of hyaluronic acid contamination that is less than 200 ng/ml (e.g. ≤150 ng/ml, ≤100 ng/ml, ≤90 ng/ml, ≤80 ng/ml, ≤75 ng/ml, ≤60 ng/ml, ≤50 ng/ml, ≤40 ng/ml, ≤25 ng/ml, ≤20 ng/ml, ≤10 ng/ml etc.). Typically, the level of hyaluronic acid contamination is less than 100 ng/ml, particularly less than 80 ng/ml. The level of hyaluronic acid contamination may also be expressed in terms of the weight of hyaluronic acid relative to the total weight of the composition. In this way, the invention provides composition comprising GAS carbohydrate from *Streptococcus pyogenes*, wherein the composition comprises a level of hyaluronic acid contamination that is less than 5% (e.g. ≤4%, ≤3%, ≤2%, ≤1%, ≤0.75%, ≤0.5%, ≤0.25%, ≤0.1% etc.) by weight of hyaluronic acid relative to the weight of GAS carbohydrate. Typically, the level of hyaluronic acid contamination is less than 1% by weight of hyaluronic acid relative to the weight of GAS carbohydrate. Levels lower than this, e.g. equal to or less than 0.005% by weight of hyaluronic acid relative to the weight of GAS carbohydrate are also obtainable.

The invention also provides a composition comprising GAS carbohydrate from *Streptococcus pyogenes*, wherein the composition comprises a level of polyrhamnose contamination that is less than 50% (e.g. ≤40%, ≤30%, ≤25%, ≤20%, ≤15%, ≤10%, ≤8%, ≤6%, ≤5%, ≤4%, ≤2%, ≤1% etc.) by weight of polyrhamnose relative to the weight of GAS carbohydrate. Typically, the level of polyrhamnose contamination is less than 20% by weight of polyrhamnose relative to the weight of GAS carbohydrate. Levels lower than this, e.g. equal to or less than 5% by weight of polyrhamnose relative to the weight of GAS carbohydrate are also obtainable.

The invention also provides a composition comprising GAS carbohydrate from *Streptococcus pyogenes*, wherein the composition comprises a level of protein contamination that is less than 4.0% (e.g. ≤3.5%, ≤3.1%, ≤3.0%, ≤2.5%, ≤2.0%, ≤1.5%, ≤1.0%, etc.) by weight of protein relative to the weight of GAS carbohydrate. Typically, the level of protein contamination is around 2% by weight of protein relative to the weight of GAS carbohydrate.

The invention also provides a composition comprising GAS carbohydrate from *Streptococcus pyogenes*, wherein the composition comprises a level of nucleic acid contamination that is less than 5% (e.g. ≤4%, ≤3%, ≤2%, ≤1%, ≤0.75%, ≤0.5%, ≤0.25%, ≤0.1% etc.) by weight of nucleic acid relative to the weight of GAS carbohydrate. Typically, the level of nucleic acid contamination is less than 1% by weight of nucleic acid relative to the weight of GAS carbohydrate. Levels lower than this, e.g. less than 0.5% by weight of nucleic acid relative to the weight of GAS carbohydrate are also obtainable.

The invention also provides a composition comprising GAS carbohydrate from *Streptococcus pyogenes*, wherein (a) the level of hyaluronic acid contamination is less than 200 ng/ml or 5% (as described above); (b) the level of polyrhamnose contamination is less than 50% (as described above); (c) the level of protein contamination is less than 4.0% (as described above), and (d) the level of nucleic acid contamination that is less than 5% (as described above).

The GAS Carbohydrate

The *S. pyogenes* GAS carbohydrate (also known as the GAS cell wall polysaccharide, or GASP) typically features a branched structure with an L-rhamnopyranose (Rhap) backbone consisting of alternating alpha-(1→2) and alpha-(1→3) links and D-N-acetylglucosamine (GlcpNAc) residues beta-(1→3)-connected to alternating rhamnose rings (FIG. 1 and [14]). Group A variant streptococci have been described wherein the Rhap backbone is present but there are no GlcpNAc branches (i.e. polyrhamnose, FIG. 2 and [6]). The invention preferably involves GAS carbohydrate from *S. pyogenes* rather than Group A variant streptococci. Indeed, the purification process of the present invention is particularly effective at reducing polyrhamnose contamination of GAS carbohydrate from *S. pyogenes*.

Saccharides purified according to the invention will generally be in their native form, but they may have been modified. For example, the saccharide may be shorter than the native GAS carbohydrate, or may be chemically modified.

Thus the saccharide used according to the invention may be a substantially full-length GAS carbohydrate, as found in nature, or it may be shorter than the natural length. Full-length polysaccharides may be depolymerised to give shorter fragments for use with the invention e.g. by hydrolysis in mild acid, by heating, by sizing chromatography, etc. A short fragment thought to correspond to the terminal unit on the GAS carbohydrate has been proposed for use in a vaccine [15]. Accordingly, short fragments are envisaged in the present invention. However, it is preferred to use saccharides of substantially full-length. Saccharides purified according to the invention typically have a molecular weight of about 10, in particular about 7.5-8.5 kDa. Molecular masses can be measured by HPLC, for example SEC-HPLC using a TSK Gel G3000SW column (Sigma) relative to pullulan standards, such as those available from Polymer Standard Service [16]. Typical conditions for this measurement involve isocratic elution with an elution buffer comprising 100 mM NaPi, 100 mM NaCl and 5% acetonitrile at a flow rate of 0.5 ml/min. The presence of GAS carbohydrate can be detected by measuring absorbance at 214 nm.

The saccharide may be chemically modified relative to the GAS carbohydrate as found in nature. For example, the saccharide may be de-N-acetylated (partially or fully), N-propionated (partially or fully), etc. The effect of de-acetylation etc., for example on immunogenicity, can be assessed by routine assays.

Starting Material

The process of the invention typically starts with the GAS carbohydrate in aqueous form, for example as an aqueous suspension, further comprising hyaluronic acid and/or polyrhamnose. Streptococcal proteins and/or nucleic acids may be present in the suspension. Typically, the suspension will comprise hyaluronic acid, polyrhamnose, proteins and nucleic acids. The hyaluronic acid will usually be derived from the *Streptococcus pyogenes* capsular polysaccharide.

Typically, the starting material will be prepared by treating the bacteria themselves (or material containing the bacterial call wall), such that the GAS carbohydrate is released. For example, bacteria can be harvested from a bacterial culture, preferably at stationary phase. The culture may be heat deactivated prior to harvesting. For example, the inventors have found that heat treatment at 90° C. for 60 min is suitable for deactivation of the culture. The harvesting may comprise centrifuging the culture and resuspending the bacterial pellet, for example in water or a saline buffer. Prior to centrifugation, the culture may be treated by tangential flow filtration, for example using a 0.2 µm hollow-fiber cartridge filter [8]. The centrifugation may be carried out at any suitable speed, e.g. at between 100 and 10,000 g. A speed of 300 g has been found to be effective. A speed of 3000 g is mentioned in ref. 8. If bacteria are resuspended in saline buffer, the suspension may be diluted with water before further treatment [8].

GAS carbohydrate can be released from the bacteria by various methods, including chemical, physical or enzymatic treatment. A typical chemical treatment is reductive acid treatment, e.g. using sodium nitrite and glacial acetic acid [e.g. as described in refs. 4, 5, 7 and 10], which releases the GAS carbohydrate from the bacteria. Typically, equal volumes of 4 N sodium nitrate and glacial acetic acid are added to the bacterial suspension and the mixture stirred for a suitable length of time, e.g. 1 hour. The treatment is carried out at a suitable temperature, e.g. 37° C. The final pH of the mixture is typically around 3.0. The pH of the mixture may be neutralised to around 6 to 7, e.g. using 4M sodium hydroxide. The mixture may be diluted with water [8].

Filtration and Ultrafiltration

The GAS carbohydrate obtained after culture, for example by the reductive acid treatment discussed above, will generally be impure and will be contaminated with hyaluronic acid and/or polyrhamnose. Streptococcal proteins and/or nucleic acids may also be present. One or more filtration step(s) may be used to purify the GAS carbohydrate by removing high molecular weight species. For example, the inventors have found that a filtration step involving orthogonal filtration can be used to remove impurities from the GAS carbohydrate, which is retained in the filtrate. Typically, the orthogonal filtration is carried out using a 0.65 µm filter. For example, a Sartopure GF2™ (Sartorius) capsule (with a 0.2 m² area) may be used. However, a 0.2 µm filter may also be used. To improve yield, any residual filtrate may be removed from the filter and combined with the rest of the filtrate. This removal can be done, for example, by applying a driving force (e.g. peristaltic or pressure) to the filter or by feeding the system with distilled water.

One or more ultrafiltration step(s) may also be used to purify the GAS carbohydrate by removing low molecular weight species. The ultrafiltration may also concentrate the GAS carbohydrate. Preferably, the one or more ultrafiltration step(s) are performed after the above filtration step(s). The inventors have found that a diafiltration step, for example by tangential flow filtration, is particularly effective for removing impurities from the GAS carbohydrate, which is retained in the retentate. The GAS carbohydrate solution may be concentrated, e.g. about 15-20 times, prior to diafiltration. The tangential flow filtration is suitably carried out against 1M NaCl (e.g. against about 10 volumes) and then water (e.g. against another 10 volumes). The tangential flow filtration may be carried out against water using a 3, 5, 10 or 30 kDa cut-off membrane. For example, a Hydrosart™ (Sartorius) 5 kDa cut-off membrane (with a 0.1 m² membrane area) may be used. Hydrosart™ is a stabilized cellulose membrane that is hydrophilic and is stable over a broad pH range. However, the inventors have found that tangential flow filtration using a 30 kDa cut-off membrane is more suitable for large-scale processes. This tangential flow filtration also allows better protein contamination removal and shorter filtration times, without substantial loss of GAS carbohydrate. After tangential flow filtration, the retentate may be concentrated, e.g. about 5 times. To improve yield, the membrane may be washed, e.g. twice, with distilled water corresponding to the membrane dead volume and the washings added to the retentate.

After filtration and/or ultrafiltration, the GAS carbohydrate preparation may be concentrated. Typically, the GAS carbohydrate preparation is diafiltered against water before further treatment.

Anionic Exchange Chromatography

The process of the invention comprises a step of anionic exchange chromatography. The inventors have found that anionic exchange chromatography is particularly effective at removing hyaluronic acid, protein and nucleic acid contamination of GAS carbohydrate, while maintaining a good yield of the saccharide.

The anionic exchange chromatography step may be performed after the filtration and/or ultrafiltration steps discussed above.

The anionic exchange chromatography may be carried out using any suitable anionic exchange matrix. Commonly used anion exchange matrices are resins such as Q-resins (based on quaternary amines) and DEAE resins (based on diethylaminoethane). The present inventors have found that Q-resins (e.g. Q-Sepharose™ XL or Q-Sepharose™ FF resins (GE Healthcare)) are particularly suitable, although other resins may be used. An appropriate amount of resin for the amount of material to be purified can be determined by routine experiments without undue burden. For example, the inventors have found that 1 mL of resin for every 0.5 mg or 1 mg of GAS carbohydrate may be effective.

Appropriate starting buffers and mobile phase buffers for the anionic exchange chromatography can also be determined by routine experiments without undue burden. Typical buffers for use in anionic exchange chromatography include N-methyl piperazine, piperazine, L-histidine, bis-Tris, bis-Tris propane, triethanolamine, Tris, N-methyl-diethanolamine, diethanolamine, 1,3-diaminopropane, ethanolamine, piperidine and phosphate buffers. The inventors have found that, advantageously, the anionic exchange chromatography step can be performed under conditions that allow "flow through" of the GAS carbohydrate, wherein impurities bind to the anion exchange matrix while GAS carbohydrate flows straight through the system into the eluant. The use of these conditions simplifies the purification process, as there is no need to use a mobile phase buffer of increasing ionic strength or increasing pH etc. to elute the GAS carbohydrate from the matrix. Appropriate conditions for flow through anionic exchange chromatography can be determined by routine experiments without undue burden. Phosphate buffers, e.g. a sodium phosphate buffer, may be suitable for the mobile phase for the anionic exchange chromatography. The buffer may be at any suitable concentration. For example, 10 mM sodium phosphate has been found to be suitable.

The inventors have found that adding alcohol to the mobile phase buffer may increase the yield of GAS carbohydrate. The inventors have also found that alcohol in the mobile phase buffer may reduce cloudiness in the GAS carbohydrate preparation. However, the inventors have found that using a mobile phase buffer that does not contain any alcohol is more suitable for large-scale processes. When used, any suitable concentration of alcohol may be present in the mobile phase buffer. For example, the alcohol may be added to the mobile phase buffer to give a final alcohol concentration of between 5% and 50% (e.g. around 10%, 15%, 20%, 25%, 30%) by volume. Typically, the alcohol is added to the mobile phase buffer to give a final alcohol concentration of between 15% and 25%, particularly 20%, by volume. The alcohol is preferably a lower alcohol, such as methanol, ethanol, propan-1-ol, propan-2-ol, butan-1-ol, butan-2-ol, 2-methyl-propan-1-ol, 2-methyl-propan-2-ol, diols, etc. The selection of an appropriate alcohol can be tested empirically, without undue burden, but alcohols such as ethanol and isopropanol (propan-2-ol) are preferred, rather than alcohols such as phenol. Typically, the alcohol will be ethanol. The alcohol may be added in pure form or may be added in a form diluted with a miscible solvent (e.g. water). Preferred solvent mixtures are alcohol:water mixtures, with a preferred ratio of between around 70:30 and around 95:5 (e.g. 75:25, 80:20, 85:15, 90:10).

Eluant fractions containing GAS carbohydrate may be determined by measuring UV absorption at 215 nm. The eluted material is highly purified relative to the GAS carbohydrate preparation before the anionic exchange chromatography step. All fractions containing GAS carbohydrate may be combined before further treatment.

The anionic exchange chromatography step may be repeated, e.g. 1, 2, 3, 4 or 5 times. However, typically the anionic exchange chromatography step will be carried out once.

Gel Filtration

The process of the invention may involve one or more step(s) of gel filtration. This gel filtration is used to select GAS carbohydrate molecules of a particular length and to further reduce contamination, particularly by proteins. However, the inventors have found that contrary to ref. 6, a gel filtration step is not required to obtain GAS carbohydrate of high purity. Accordingly, this step may be omitted from the processes of the invention. Omitting this step may facilitate scalability of the process.

For example, gel filtration step(s) may be carried out after the anionic exchange chromatography step discussed above.

The gel filtration step(s) may be carried out using any suitable gel filtration matrix. Commonly used gel filtration matrices are based on dextran gels, agarose gels, polyacrylamide gels, polyacryloylmorpholine gels, and polystyrene gels etc. Cross-linked dextran gels and mixed polyacrylamide/agarose gels may also be used. The present inventors have found that dextran gels (e.g. a Sephacryl S100 gel or a Sephadex™ G50 gel (both GE Healthcare)) are particularly suitable, although other gels may be used. An appropriate amount of gel for the amount of material to be purified can be determined by routine experiments without undue burden. For example, the inventors have found that 1 mL of gel for every 0.2 mg of GAS carbohydrate may be effective. Similarly, an appropriate amount of GAS carbohydrate preparation for any given gel filtration column can be determined by routine experiments without undue burden. Typically, the volume of GAS carbohydrate preparation applied to the gel filtration column will not exceed 5% of the column volume.

Appropriate mobile phase buffers for the gel filtration can be determined by routine experiments without undue burden. Typical buffers for use in gel filtration include N-methyl piperazine, piperazine, L-histidine, bis-Tris, bis-Tris propane, triethanolamine, Tris, N-methyl-diethanolamine, diethanolamine, 1,3-diaminopropane, ethanolamine, piperidine and phosphate buffers. For example, phosphate buffers, e.g. a sodium phosphate buffer, may be suitable for the mobile phase. The buffer may be at any suitable concentration. For example, 10 mM sodium phosphate may be used for the mobile phase.

The inventors have found that, advantageously, the gel filtration can be performed using the same mobile phase buffer as the anionic exchange chromatography step. The use of this buffer simplifies the purification process, as there is no need to prepare a different buffer. For example, a 10 mM sodium phosphate buffer may be used for the mobile phase of both steps.

Once again, it is preferred to add an alcohol to the mobile phase buffer for the gel filtration. This addition may increase the yield of GAS carbohydrate and/or reduce cloudiness in the GAS carbohydrate preparation. Any suitable concentration of alcohol may be used in the mobile phase buffer. For example, the alcohol may be added to the mobile phase buffer to give a final alcohol concentration of between 5% and 50% (e.g. around 10%, 15%, 20%, 25%, 30%) by volume. Typically, the alcohol is added to the mobile phase buffer to give a final alcohol concentration of between 15 and 25, particularly 20%, by volume. The alcohol is preferably a lower alcohol, such as methanol, ethanol, propan-1-ol, propan-2-ol, butan-1-ol, butan-2-ol, 2-methyl-propan-1-ol, 2-methyl-propan-2-ol, diols, etc. The selection of an appropriate alcohol can be tested empirically, without undue burden, but alcohols such as ethanol and isopropanol (propan-2-ol) are preferred, rather than alcohols such as phenol. Typically, the alcohol will be ethanol. The alcohol may be added in pure form or may be added in a form diluted with a miscible solvent (e.g. water). Preferred solvent mixtures are alcohol:water mixtures, with a preferred ratio of between around 70:30 and around 95:5 (e.g. 75:25, 80:20, 85:15, 90:10).

Eluant fractions containing GAS carbohydrate may be determined by measuring UV absorption at 215 nm. The inventors have found that the GAS carbohydrate may be present in the eluant as two peaks: one peak corresponding to high molecular weight GAS carbohydrate saccharides and another (often smaller) peak corresponding to low molecular weight GAS carbohydrate saccharides. Typically, the fractions containing the high molecular weight GAS carbohydrate saccharides are chosen if the GAS carbohydrate preparation is to be processed for subsequent vaccine preparation. Alternatively, fractions containing both the high and low molecular weight GAS carbohydrate saccharides may be pooled before further treatment.

The GAS carbohydrate preparation may be diafiltered against water before further treatment.

Concentration

In addition to, or instead of, the one or more step(s) of gel filtration, the process of the invention may involve one or more steps of concentrating the GAS carbohydrate. This concentration is useful for obtaining a sample of the correct concentration for subsequent conjugation of the GAS carbohydrate to a carrier molecule, as described below. However, the inventors have found that this concentration step is not required to obtain GAS carbohydrate of high purity. Accordingly, this step may be omitted from the processes of the invention.

The inventors have found that using one or more steps of concentrating the GAS carbohydrate is more suitable than using gel filtration for large-scale processes. The use of one or more steps of concentrating the GAS carbohydrate is particularly suitable when the GAS carbohydrate has been purified by tangential flow filtration using a 30 kDa cut-off membrane as described above. The inventors have found that the use of this tangential flow filtration step means that it is not necessary to include gel filtration step(s) in the process to remove impurities from the GAS carbohydrate, particularly polyrhamnose.

For example, concentration step(s) may be carried out after the anionic exchange chromatography step discussed above. If used in addition to the gel filtration step(s) discussed above, the concentration step(s) may be carried out before or after the gel filtration step(s) discussed above. However, typically, concentration step(s) are used instead of gel filtration step(s).

The concentration step(s) may be carried out by any suitable method. For example, the inventors have found that the concentration step(s) may be ultrafiltration step(s) as described above, for example tangential flow filtration using a 5 or 10 kDa cut-off membrane. For example, a Hydrosart™ (Sartorius) 10 kDa cut-off membrane (with a 200 cm$^2$ membrane area) may be used. Typically, a Hydrosart™ (Sartorius) 5 kDa cut-off membrane (with a 200 cm$^2$ membrane area) is used. The inventors have found that a 5 kDa cut-off membrane may provide a higher yield than a 10 kDa cut-off membrane. Without wishing to be bound by theory, it is thought that a 5 kDa membrane provides a cut-off that is further from the mass of the GAS carbohydrate and consequentially a higher yield.

The GAS carbohydrate preparation may be diafiltered against water before further treatment. However, the inventors have found that further diafiltration may result in loss of GAS carbohydrate in the permeate.

Further Treatment of the GAS Carbohydrate

After purification, the saccharide may be further treated to remove contaminants. This is particularly important in situations where even minor contamination is not acceptable (e.g. for human vaccine production).

The saccharide may be subjected to vacuum drying. This treatment will typically be used not to stabilise the saccharide for storage, but to dry the saccharide and remove any residual alcohol.

Further rounds of filtration can also be performed.

The purified GAS carbohydrate typically has a degree of polymerisation of between 10 and 30, e.g. between 20 and 24 (as measured by the concentration of aldehyde groups in the purified sample [17]). However, this polysaccharide may be depolymerised to form oligosaccharides. Oligosaccharides may be preferred to polysaccharides for use in vaccines. Depolymerisation from polysaccharide to oligosaccharide can occur before or after the anionic exchange chromatography step. If depolymerisation is performed, the products will generally be sized in order to remove short-length oligosaccharides. This can be achieved in various ways, such as ultrafiltration followed by ion-exchange chromatography. Where the composition of the invention includes a depolymerised saccharide, it is preferred that depolymerisation precedes any conjugation.

If D-N-acetylglucosamine residues in the native GAS carbohydrate have been de-N-acetylated then the processes of the invention may include a step of re-N-acetylation. Controlled re-N-acetylation can conveniently be performed using a reagent such as acetic anhydride ($CH_3CO)_2O$ e.g. in 5% ammonium bicarbonate [18].

These additional steps can generally be performed at room temperature.

Storage

The GAS carbohydrate preparation may be lyophilised, e.g. by freeze-drying under vacuum, or frozen in solution (e.g. as the eluent from the final concentration step, if included) for storage at any stage during the purification process. Accordingly, it is not necessary for the preparation to be transferred immediately from one step of the process to another. For example, if the GAS carbohydrate preparation is to be purified by filtration and/or ultrafiltration, then it may be lyophilised or frozen in solution prior to this purification. Similarly, the GAS carbohydrate may be lyophilised or frozen in solution prior to the anionic exchange chromatography step. If the GAS carbohydrate preparation is to be purified by gel filtration, then it may be lyophilised or frozen in solution prior to this step. Similarly, if the GAS carbohydrate preparation is to be concentrated, then it may be lyophilised or frozen in solution prior to this step. The lyophilised preparation is reconstituted in an appropriate solution prior to further treatment. Similarly, the frozen solution is defrosted prior to further treatment.

The purified GAS carbohydrate obtained by the process of the invention may be processed for storage in any suitable way. For example, the saccharide may be lyophilised as described above. Alternatively, the saccharide may be stored in aqueous solution, typically at low temperature, e.g. at −20° C. Conveniently, the saccharide may be stored as the eluant from the anionic exchange chromatography, gel filtration or concentration steps.

Conjugation

The final purified GAS carbohydrate of the invention can be used as an antigen without further modification e.g. for use in in vitro diagnostic assays, for use in immunisation, etc.

For immunisation purposes, however, it is preferred to conjugate the saccharide to a carrier molecule, such as a protein. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 19] and is a well known technique [e.g. reviewed in refs. 20 to 28]. Thus the processes of the invention may include the further step of conjugating the purified GAS carbohydrate to a carrier molecule, e.g. a carrier protein.

In one aspect, the invention therefore provides a conjugate of (i) a GAS carbohydrate obtainable by the process of the invention and (ii) a carrier molecule.

The carrier molecule may be covalently conjugated to the GAS carbohydrate directly or via a linker:

Direct linkages of GAS carbohydrate to carrier proteins has been reported e.g. in refs. 6 and 8. The typical prior art process for GAS carbohydrate conjugation involves reductive amination of a purified saccharide to a carrier protein such as tetanus toxoid (TT) [e.g. as discussed in ref. 8 by reference to ref. 29]. The reductive amination involves an amine group on the side chain of an amino acid in the carrier and an aldehyde group in the saccharide. The GAS carbohydrate saccharide includes an aldehyde group at a terminal residue. Accordingly, this group may be used for conjugation to the carrier [e.g. as discussed in ref. 8]. Alternatively, additional aldehyde groups may be generated before conjugation, for example by oxidation of the non-reducing end of the saccharide.

Linkages via a linker group may be made using any known procedure, for example, the procedures described in references 30 and 31. A preferred type of linkage is an adipic acid linker, which may be formed by coupling a free —NH$_2$ group (e.g. introduced to a GAS carbohydrate by amination) with adipic acid (using, for example, diimide activation), and then coupling a protein to the resulting saccharide-adipic acid intermediate [32, 33, 34]. Another preferred type of linkage is a carbonyl linker, which may be formed by reaction of a free hydroxyl group of a modified GAS carbohydrate with CDI [35, 36] followed by reaction with a protein to form a carbamate linkage. Other linkers include β-propionamido [37], nitrophenyl-ethylamine [38], haloacyl halides [39], glycosidic linkages [40], 6-aminocaproic acid [41], N-succinimidyl-3-(2-pyridyldithio)-propionate (SPDP) [42], adipic acid dihydrazide ADH [43], $C_4$ to $C_{12}$ moieties [44], etc. Carbodiimide condensation can also be used [45]. An alternative conjugation process involves the use of —NH$_2$ groups in the saccharide (either from de-N-acetylation, or after introduction of amines) in conjunction with bifunctional linkers, as described for GBS capsular saccharide in ref. 46.

Other suitable processes for GAS carbohydrate conjugation are discussed in ref. 6.

Preferred carrier proteins are bacterial toxins, such as diphtheria or tetanus toxins, or toxoids or mutants thereof. These are commonly used in conjugate vaccines. The $CRM_{197}$ diphtheria toxin mutant is particularly preferred [47].

Other suitable carrier proteins include the N. meningitidis outer membrane protein complex [48], synthetic peptides [49,50], heat shock proteins [51,52], pertussis proteins [53, 54], cytokines [55], lymphokines [55], hormones [55], growth factors [55], human serum albumin (preferably recombinant), artificial proteins comprising multiple human CD4$^+$ T cell epitopes from various pathogen-derived antigens [56] such as N19 [57], protein D from H. influenzae [58-60], pneumolysin [61] or its non-toxic derivatives [62], pneumococcal surface protein PspA [63], iron-uptake proteins [64], toxin A or B from C. difficile [65], recombinant Pseudomonas aeruginosa exoprotein A (rEPA) [66], a GBS protein [112], a GAS protein [67] etc.

Attachment to the carrier is preferably via a —NH$_2$ group e.g. in the side chain of a lysine residue in a carrier protein, or of an arginine residue. Attachment may also be via a —SH group e.g. in the side chain of a cysteine residue.

It is possible to use more than one carrier protein for the GAS carbohydrate antigen e.g. to reduce the risk of carrier suppression. Thus GAS carbohydrate saccharides might be in two groups, with some conjugated to $CRM_{197}$ and others conjugated to tetanus toxoid. In general, however, it is preferred to use the same carrier protein for all saccharides.

A single carrier protein might carry more than one saccharide antigen [68, 69].

Conjugates with a saccharide:protein ratio (w/w) of between 1:10 (i.e. excess protein) and 10:1 (i.e. excess saccharide) are preferred. Ratios between 1:5 and 5:1 are preferred, as are ratios between 1:5 and 1:2.5.

Conjugates may be used in conjunction with free carrier [70]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated saccharides can be separated. There are many suitable methods, including hydrophobic chromatography, tangential ultrafiltration, diafiltration etc. [see also refs. 71 & 72, etc.].

Combinations of Conjugates and Other Antigens

Saccharides prepared by the methods of the invention (in particular after conjugation as described above) can be mixed e.g. with each other and/or with other antigens. Thus the processes of the invention may include the further step of mixing the saccharide with one or more further antigens.

Multiple different GAS carbohydrate conjugates may be mixed. The composition will be produced by preparing separate conjugates and then combining the conjugates.

The further antigen(s) may comprise antigens from non-GAS pathogens. Thus the compositions of the invention may further comprise one or more non-GAS antigens, including additional bacterial, viral or parasitic antigens. These may be selected from the following:

- a protein antigen from *N. meningitidis* serogroup B, such as those in refs. 73 to 79, with protein '287' (see below) and derivatives (e.g. 'AG287') being particularly preferred.
- an outer-membrane vesicle (OMV) preparation from *N. meningitidis* serogroup B, such as those disclosed in refs. 80, 81, 82, 83 etc.
- a saccharide antigen from *N. meningitidis* serogroup A, C, W135 and/or Y, such as the oligosaccharide disclosed in ref. 84 from serogroup C or the oligosaccharides of ref. 85.
- a saccharide antigen from *Streptococcus pneumoniae* [e.g. refs. 86-88; chapters 22 & 23 of ref. 95].
- an antigen from hepatitis A virus, such as inactivated virus [e.g. 89, 90; chapter 15 of ref. 95].
- an antigen from hepatitis B virus, such as the surface and/or core antigens [e.g. 90,91; chapter 16 of ref. 95].
- an antigen from hepatitis C virus [e.g. 92].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 93 & 94; chapter 21 of ref. 95].
- a diphtheria antigen, such as a diphtheria toxoid [e.g. chapter 13 of ref. 95].
- a tetanus antigen, such as a tetanus toxoid [e.g. chapter 27 of ref. 95].
- a saccharide antigen from *Haemophilus influenzae* B [e.g. chapter 14 of ref. 95]
- an antigen from *N. gonorrhoeae* [e.g. 73, 74, 75].
- an antigen from *Chlamydia pneumoniae* [e.g. 96, 97, 98, 99, 100, 101, 102].
- an antigen from *Chlamydia trachomatis* [e.g. 103].
- an antigen from *Porphyromonas gingivalis* [e.g. 104].
- polio antigen(s) [e.g. 105, 106; chapter 24 of ref. 95] such as IPV.
- rabies antigen(s) [e.g. 107] such as lyophilised inactivated virus [e.g.108, RabAvert™]
- measles, mumps and/or rubella antigens [e.g. chapters 19, 20 and 26 of ref. 95].
- influenza antigen(s) [e.g. chapters 17 & 18 of ref. 95], such as the haemagglutinin and/or neuraminidase surface proteins.
- an antigen from *Moraxella catarrhalis* [e.g. 109].
- an antigen from *Streptococcus agalactiae* (group B *streptococcus*) [e.g. 67, 110-112].

Where a saccharide or carbohydrate antigen is used, it is preferably conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of pertussis toxin by chemical and/or genetic means [94]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens may be adsorbed to an aluminium salt.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 113 to 121]. Protein components of the compositions of the invention may thus be replaced by nucleic acid (preferably DNA e.g. in the form of a plasmid) that encodes the protein.

In practical terms, there may be an upper limit to the number of antigens included in compositions of the invention. The number of antigens in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3.

Pharmaceutical Compositions and Methods

The invention provides processes for preparing pharmaceutical compositions, comprising the steps of mixing (a) a saccharide of the invention (optionally in the form of a conjugate) with (b) a pharmaceutically acceptable carrier. A thorough discussion of such carriers is available in reference 122.

The compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 123].

The pharmaceutical composition is preferably sterile. It is preferably pyrogen-free.

It is preferably buffered e.g. at between pH 6 and pH 8, generally around pH 7. The composition may be aqueous, or it may be lyophilised.

The invention also provides a delivery device containing a pharmaceutical composition of the invention. The device may be, for example, a syringe or an inhaler.

Pharmaceutical compositions of the invention are preferably immunogenic compositions, in that they comprise an immunologically effective amount of a GAS carbohydrate immunogen. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Once formulated, the compositions of the invention can be administered directly to the subject. The subjects to be treated can be animals; in particular, human subjects can be treated.

Immunogenic compositions of the invention may be used therapeutically (i.e. to treat an existing infection) or prophylactically (i.e. to prevent future infection).

The pharmaceutical compositions may be packaged into vials or into syringes. The syringes may be supplied with or without needles. A syringe will include a single dose of the composition, whereas a vial may include a single dose or multiple doses.

Aqueous compositions of saccharides of the invention are suitable for reconstituting other vaccines from a lyophilised form. Where a composition of the invention is to be used for such extemporaneous reconstitution, the invention provides a process for reconstituting such a lyophilised vaccine, comprising the step of mixing the lyophilised material with an aqueous composition of the invention. The reconstituted material can be used for injection.

General

The term "comprising" encompasses "including" as well as "consisting" e.g. a composition "comprising" X may consist exclusively of X or may include something additional e.g. X+Y.

The term "about" in relation to a numerical value x means, for example, x+10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. For example, if a saccharide has already been partially purified by removing contaminating nucleic acids and/or proteins then this step can be omitted from the processes of the invention. Similarly, a step of removing contaminants can be performed to give material ready for anionic exchange chromatography, but the anionic exchange chromatography step need not be performed. The anionic exchange chromatography step need not be performed in order to fall within the scope of the invention, as the pre-treated material has utility as an intermediate in saccharide preparation, and may be used, stored, exported, etc. for later use e.g. for later anionic exchange chromatography. These different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

MODES FOR CARRYING OUT THE INVENTION

Example 1

Purification of GAS Carbohydrate from *Streptococcus pyogenes*

Figure 1:
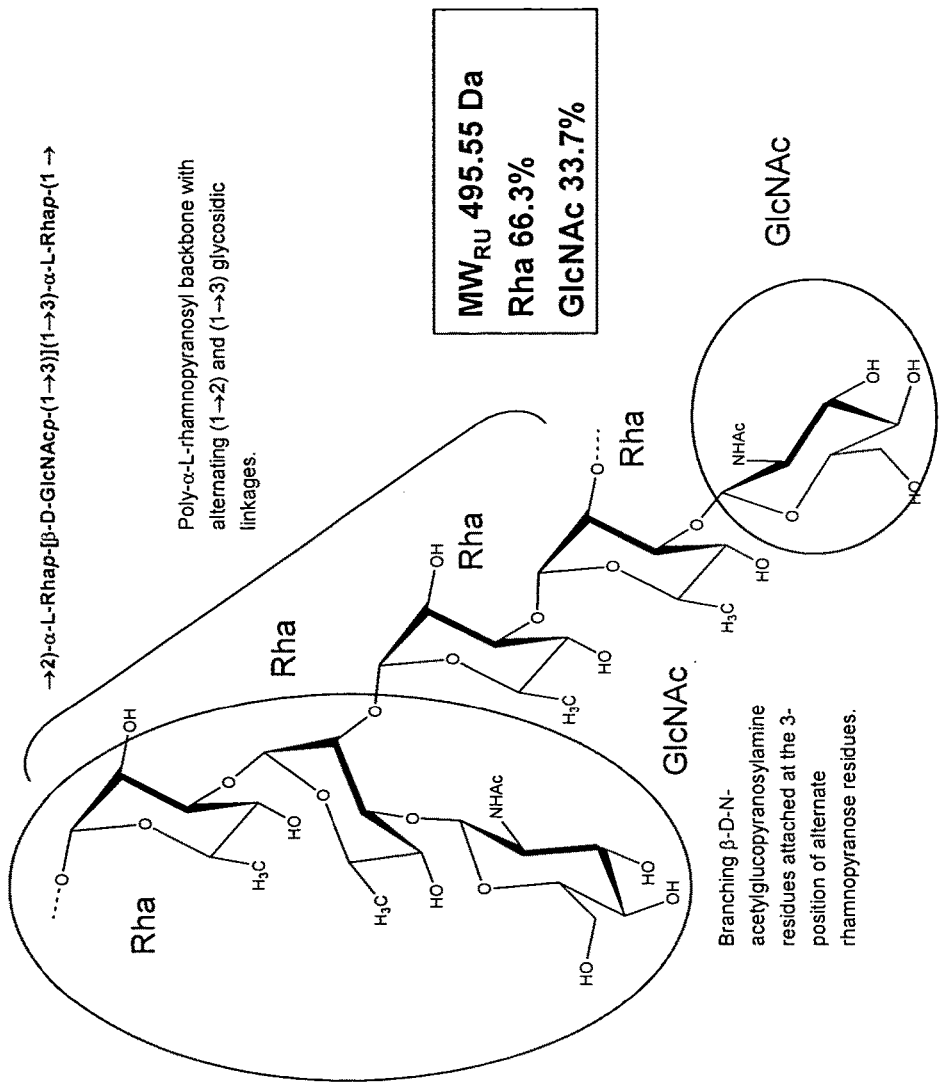
FIG. 1 illustrates the structure of the GAS carbohydrate from *S. pyogenes*.
Figure 2:
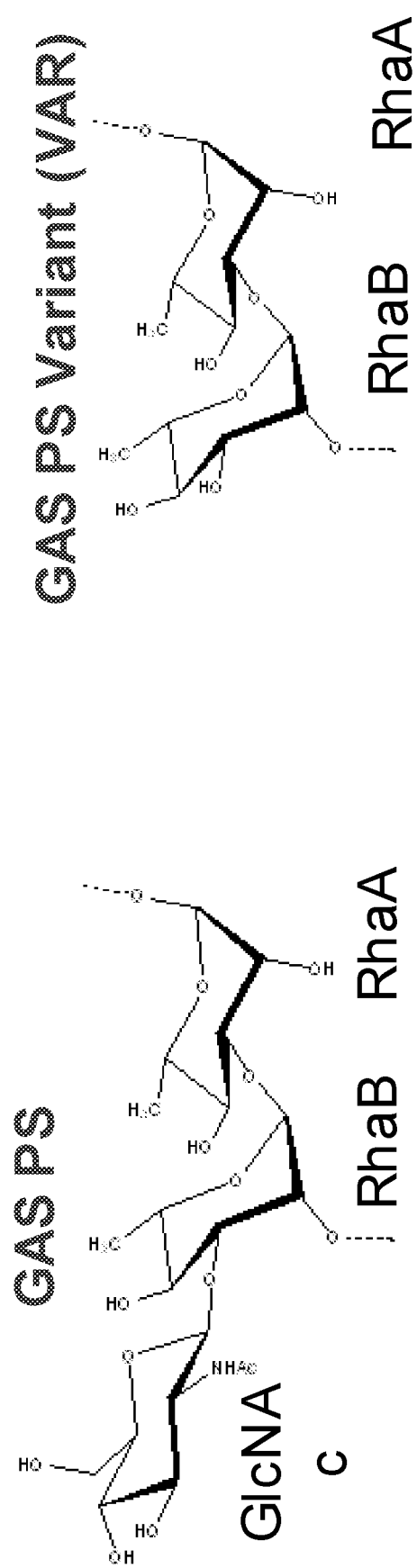
FIG. 2 compares the structure of the GAS carbohydrate from *S. pyogenes* with GAS carbohydrate from Group A variant streptococci.
Figure 3:
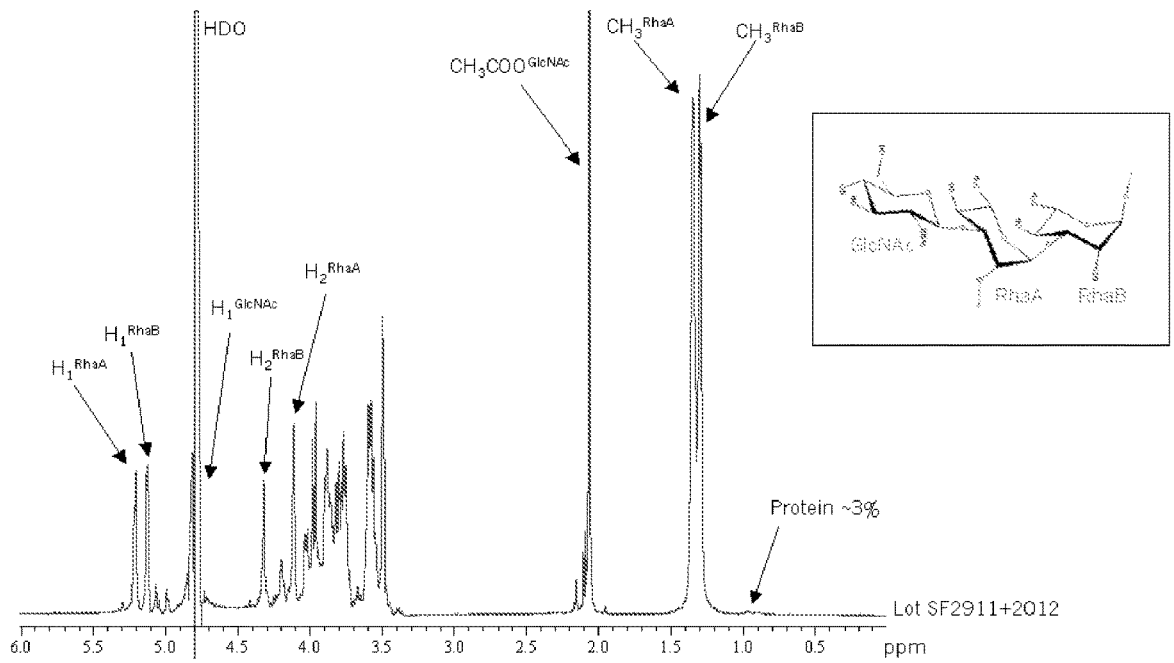
FIG. 3 shows an exemplary NMR spectrum for the GAS carbohydrate.
Figure 3:
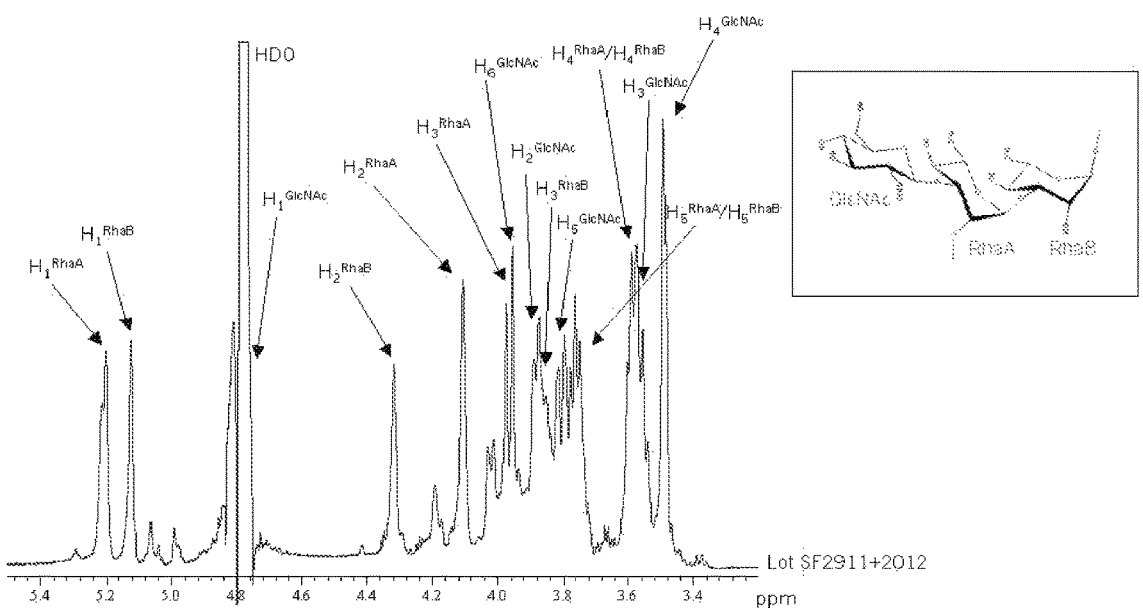

After each purification step the GAS carbohydrate structure was verified by NMR analysis (see below). An exemplary NMR spectrum for the GAS carbohydrate is presented in FIG. 3.

Step 1: GAS Carbohydrate Extraction

4 L of *Streptococcus pyogenes* bacterial growth culture was heat inactivated at 80° C. and centrifuged at 300 g. The pelleted bacteria were resuspended in saline buffer and GAS carbohydrate released by reductive acidic treatment. Briefly, 0.1 volumes of 4 N sodium nitrite and 0.1 volumes of glacial acetic acid were added to the bacterial suspension with stirring until the mixture had a final pH or around 3.0. The pH was then neutralized until it was round 6-7.

Step 2: Filtration and Ultrafiltration

The mixture was filtered using a 0.6 µm filter (Sartopure GF2, Sartorius) and then ultrafiltered using a 3 kDa cut-off membrane (with a 0.1 m$^2$ membrane area). The preparation was concentrated until it had a volume of approximately 200 mL and dialysed against water using approximately 10 volumes of water. The protein contamination of the GAS carbohydrate preparation at this stage was measured and shown to be around 20-30%.

Steps 3 and 4: Chromatographic Steps

The following chromatographic steps were performed on an AKTA™ system (Farmacia). GAS carbohydrate was detected in the eluant fractions by measuring UV absorption at 215 nm.

The GAS carbohydrate preparation was treated by anionic exchange chromatography using a Q Sepharose™ XL resin (GE Healthcare). GAS carbohydrate is collected in the column flow through. 1 mL resin was used for every 0.5 mg GAS carbohydrate. The mobile phase buffer was 10 mM sodium phosphate buffer supplemented with 20% ethanol by volume. The GAS carbohydrate appeared in the flow though as a single peak. All fractions containing the GAS carbohydrate were pooled. The protein contamination of the GAS carbohydrate preparation at this stage was measured and shown to be around 5%.

The GAS carbohydrate preparation was then treated by gel filtration using a Sephadex™ G50 gel (GE Healthcare). 1 mL gel was used for every 0.2 mg GAS carbohydrate. The GAS carbohydrate preparation volume was not allowed to exceed 5% of the volume of the gel filtration column. The mobile phase buffer was 10 mM sodium phosphate buffer supplemented with 20% ethanol by volume. The GAS carbohydrate appeared in the flow though as two peaks: a) a big peak of high molecular weight GAS carbohydrate species; and b) a small peak of low molecular weight GAS carbohydrate species. The first peak was selected for use in the preparation of vaccines. The protein contamination of the GAS carbohydrate preparation at this stage was measured and shown to be around 2-3%. The yield of GAS carbohydrate was 50-90%.

Figure 4:
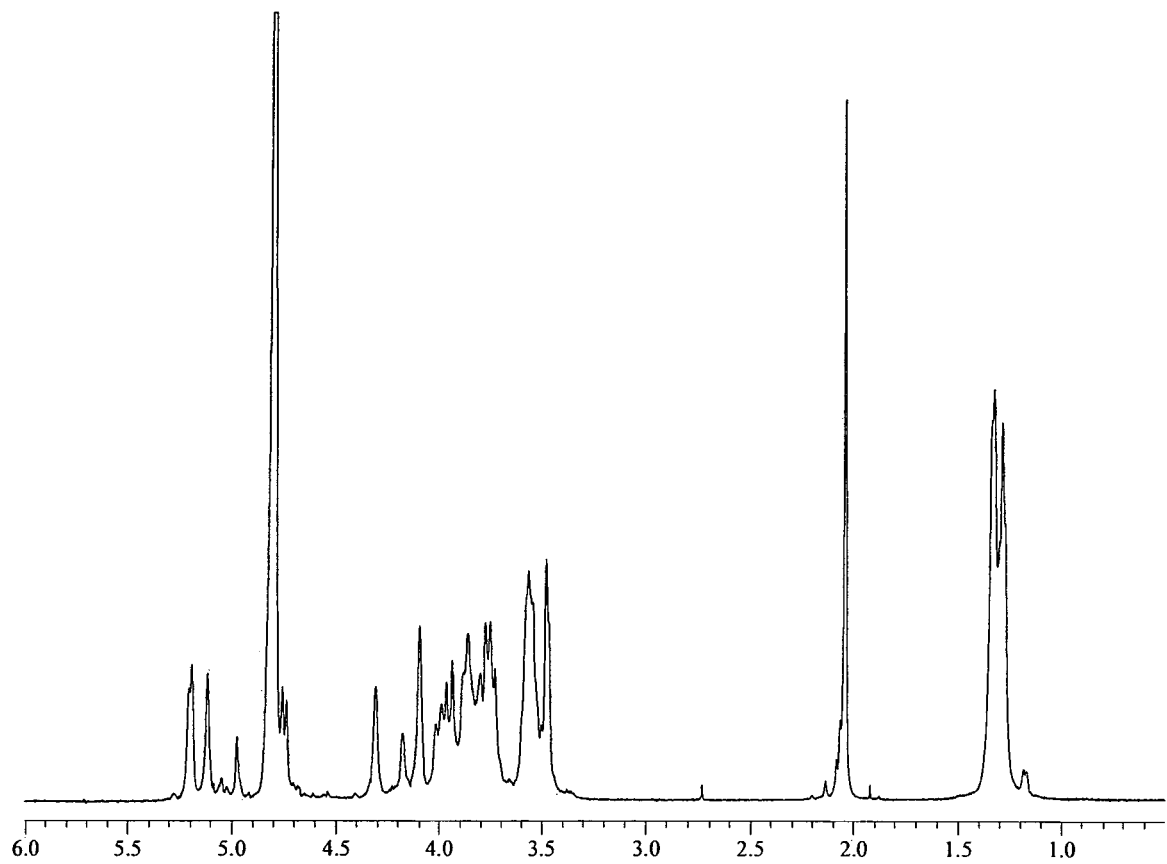
FIG. 4 shows an exemplary NMR spectrum for the GAS carbohydrate after gel filtration.

An exemplary NMR spectrum for the GAS carbohydrate after gel filtration is presented in FIG. 4. Intergration of the NMR spectrum peaks confirms that the GAS carbohydrate has the correct structure (Table I).

Storage

The GAS carbohydrate preparation was stored at −20° C.
Comparison of the Efficiency of Different Chromatographic Methods The efficiency of different types of chromatography for reducing the contamination of GAS carbohydrate preparations was compared. The chromatographic types were gel filtration (using a Sephadex™ G50 gel); anionic exchange (using a Q Sepharose™ XL resin); cationic exchange (using a SP Sepharose™ XL resin); and hydrophobic interaction (using a phenyl Sepharose™ 6 Fast Flow resin). All resins and gels were obtained from GE healthcare. The final yield of GAS carbohydrate (CHO) and the protein contamination of the GAS carbohydrate preparation obtained from each type of chromatography was measured (Table II).

TABLE II

| Chromatography/Type of resin | CHO yield, % | Final protein contamination, % w/w |
|---|---|---|
| Gel filtration/Sephadex G50 | 70 | 3.1 |
| Anionic exchange/Q sepharose XL | 77 | 2.3 |
| Cationic exchange/SP Sepharose XL | nd* | 3.7 |
| Hydrophobic interactions/Phenyl Sepharose 6 Fast Flow | 63 | nd |

*nd—not determined (interference)

These data show that anionic exchange chromatography results in a higher yield of GAS carbohydrate, particularly compared to the gel filtration used in ref. 6. The anionic exchange chromatography also results in the least amount of protein contamination of all of the methods tested.

Figure 5:
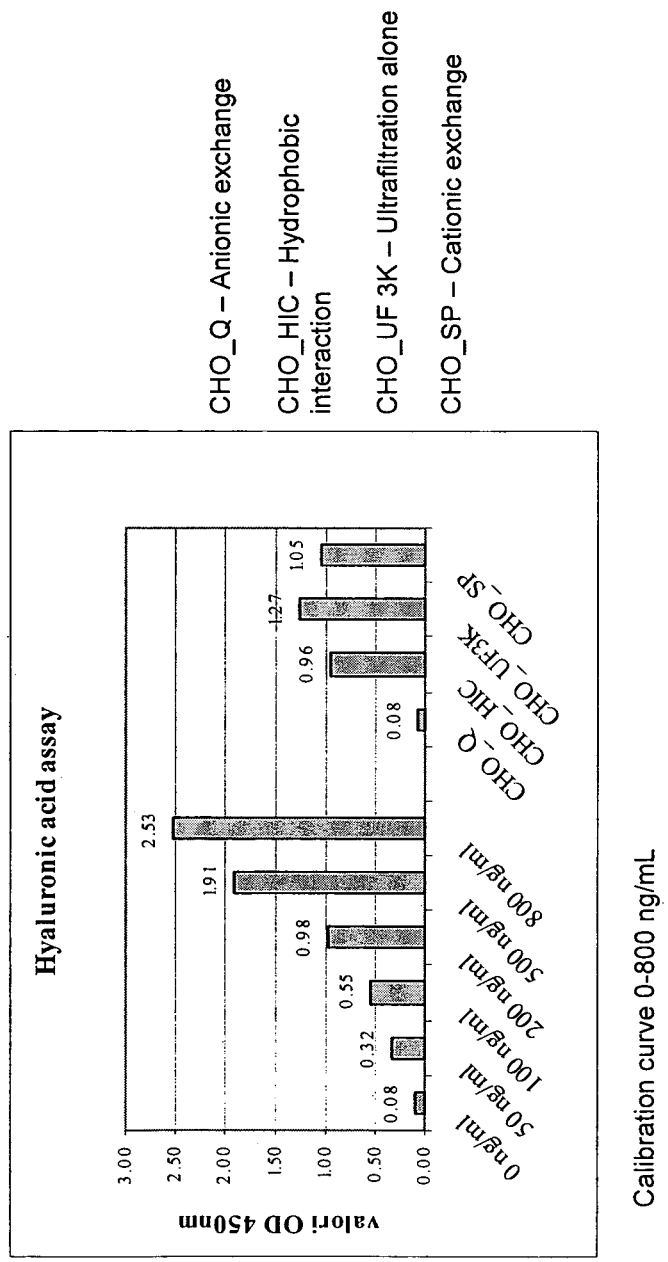
FIG. 5 compares the hyaluronic acid contamination of GAS carbohydrate preparations obtained using anionic exchange, cationic exchange and hydrophobic interaction chromatographic methods with the contamination seen after ultrafiltration with a 3 kDa cut-off membrane alone.

The hyaluronic acid contamination of the GAS carbohydrate preparations obtained from the anionic exchange, cationic exchange and hydrophobic interaction chromatographic methods was compared with the contamination seen after ultrafiltration with a 3 kDa cut-off membrane alone (FIG. 5). These data shows that anionic exchange chromatography results the least amount of hyaluronic acid contamination of all of the methods tested.

Analytical Methods

GAS Carbohydrate Concentration Measurement

High-performance anion-exchange chromatography with pulsed amperometric detection was performed using the DIONEX™ system. The GAS carbohydrate preparation was hydrolyzed in 4 M trifluoroacetic acid. A CarboPac™ PA1 analytical column was used with 50 mM NaOH as the mobile phase buffer. 500 mM NaOH was used to regenerate the column. The retention time for N-acetyl-glucosamine and rhamnose were 5.3 min and 7.2 min respectively. Peaks of rhamnose and N-acetyl-glucosamine were integrated and the amount of GAS carbohydrate calculated based on standard calibration curves.

Protein Concentration

Protein contamination was measured using a MicroBCA assay (Pierce).

Nucleic Acid Concentration

Nucleic acid concentration was measured by absorbance (A) at 260 nm. The concentration was quantified using the Lambert-Beer law of $A=\varepsilon bc$, where c is the concentration of the sample; b is the length of the sample (1 cm) and $\varepsilon$ is

TABLE I

| Sample | $H_1^{RhaA}$ (integral = mol)* | $H_1^{RhaB}$ (integral = mol)* | $H_1^{GlcNAc}$ (Integral = mol)* | $CH_3CONH^{GlcNAc}$ (integral − mol)** | $CH_3^{RhaA + RhaB}$ (integral − mol)*** |
|---|---|---|---|---|---|
| Fermentation sample (Lot 2911 + 2012) | 1.03 | 0.94 | 1.00 | 3.31 − 1.10 | 6.56 − 2.19 |
| GAS carbohydrate after ultrafiltration (lot GCII) | 0.96 | 0.95 | 1.00 | 2.96 − 0.99 | 5.94 − 1.98 |
| GAS carbohydrate after anion exchange chromatography (lot GCII) | 1.18 | 0.96 | 1.00 | 3.06 − 1.02 | 6.55 − 2.18 |
| GAS carbohydrate after gel filtration (lot GCIV) | 0.98 | 0.94 | 1.00 | 3.13 − 1.04 | 6.36 − 2.12 |

*Integral value corresponds to mol.
**Integral value corresponds to 3x mol.
***Integral value corresponds to 6x mol. The reference value was fixed as $H_1^{GlcNAc}$ or $CH_3CONH^{GlcNAc}$ when the $H_1^{GlcNAc}$ peak was not detected because of an overlap with the HDO signal.

0.020 (μg/ml)$^{-1}$ cm$^{-1}$ (the literature value for the DNA double helix). A solution of polysaccharide at 1 mg/ml in water or buffer was read in a spectrophotometer (Spectrophotometer Lambda 25 Perkin Elmer) in a quartz cuvette, resetting the instrument with corresponding water or buffer. The concentration of the nucleic acid was calculated as c=A/εb. From this value, the % of nucleic acid contamination was calculated by dividing the nucleic acid concentration with the polysaccharide concentration and multiplying the result by 100.

NMR Analysis.

Samples (~1 mg of polysaccharide) were prepared by freeze-drying to eliminate protonated H$_2$O solvent. The product was then dissolved in deuterium oxide (D$_2$O, 89.9% atom D, from Aldrich) to produce a uniform solution. The inventors have found that freeze-drying does not affect the physicochemical structure of the saccharide moiety.

1H NMR experiments were recorded at 25° C. on a Bruker Avance™ 600 MHz spectrometer, using a 5-mm broadband probe (Bruker). The XWINNMR™ software package (Bruker) was used for data acquisition and processing. 32 k data points were collected over a 10 ppm spectral width for the proton spectra. The transmitter was set at the HDO frequency, which was also used as reference signal (4.79 ppm).

1-D proton NMR spectra were collected using a standard one-pulse experiment.

Estimation of Hyaluronic Acid (HA) Residual Content.

The residual hyaluronic acid content was estimated by a commercial kit of Corgenix Inc. (Product number 029-001). This HA test kit is an enzyme-linked binding protein assay that uses a capture molecule known as hyaluronic acid binding protein (HABP). Properly diluted serum or plasma and HA reference solutions are incubated in HABP-coated microwells, allowing HA present in samples to react with the immobilized binding protein (HABP). After the removal of unbound sample molecules by washing, HABP conjugated with horseradish peroxidase (HRP) solution is added to the microwells to form complexes with bound HA. Following another washing step, a chromogenic substrate of tetramethylbenzidine and hydrogen peroxide is added to effect a colour change in the reaction mixture. The intensity of the colour is measured by optical density (OD) units with a spectrophotometer at 450 nm. HA levels in unknown and control samples are determined against a reference curve prepared from the reagent blank (0 ng/mL) and the HA reference solutions provided with the kit (50, 100, 200, 500, 800 ng/mL)

Example 2

Optimisation of Purification of GAS Carbohydrate from *Streptococcus pyogenes*

The GAS carbohydrate obtained after culture is generally impure and contaminated with hyaluronic acid, proteins, polyrhamnose and nucleic acids. The purification process of Example 1, based on tangential flow filtration, anionic exchange chromatography and size exclusion chromatography (gel-filtration), has been optimized in order to facilitate scalability and improve purity.

Figure 6:
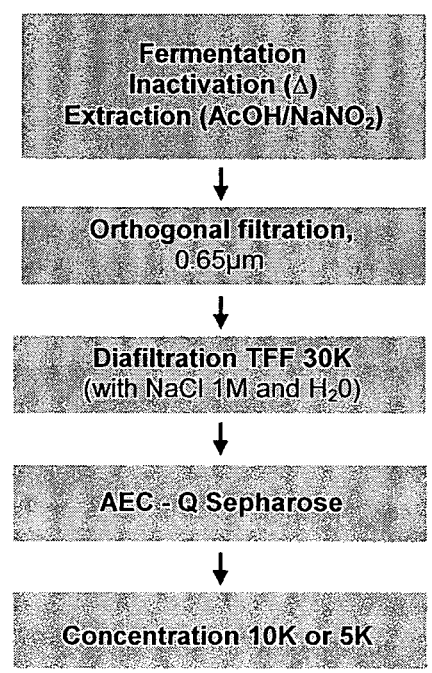
FIG. 6 summarises an optimised process for purifying GAS carbohydrate.

The optimised purification process (summarised in FIG. 6) removes hyaluronic acid, reduces polyrhamnose contamination to <20% and reduces the residual protein contamination to <4%. The sequential steps of this process are described in more detail below.

0.65 μm Orthogonal Filtration

This first purification step removes particulate contamination using 0.65 μm orthogonal filtration. Before filtration, the pH of the GAS carbohydrate suspension obtained after the sodium nitrate and glacial acetic acid treatment was neutralized to around 6 to 7. The mixture was then filtered using a Sartopure GF2™ capsule 0.65 μm (Sartorius). For a suspension of about 2 L obtained from a 5 L fermentation, a filtration surface of 0.2 m$^2$ was typically used, with the operation being completed in about 30-40 minutes.

Table III demonstrates exemplary GAS carbohydrate concentrations for the filtrate from this step.

TABLE III

| Sample | GlcNAc mg/ml | GlcNAc mgTOT |
|---|---|---|
| 9A | 0.281 | 1011.6 |
| 10 | 0.324 | 1036.48 |
| 12 | 0.239 | 812.6 |

30 kDa Tangential Flow Filtration

The second step is tangential flow filtration to remove low molecular weight species (e.g. protein, nucleic acid and hyaluronic acid). Different cut-off membranes have been compared in order to improve purification and reduce process time.

Hydrosart™ 3 kDa, 5 kDa, 10 kDa and 30 kDa cut-off membranes (Sartorius) with 0.1 m$^2$ membrane areas were used to process material from a 5 L fermentation. The crude polysaccharide solution was concentrated about 15-20 times and dialyzed first against about 10 volumes of NaCl 1M and subsequently against water using approximately 10 volumes. The tangential flow filtration step was performed using a holder for 0.1 m$^2$ cassettes (Sartorius) with a peristaltic pump (WatsonMarlon). The pressure conditions used were Pin=1.0 bar and Pout=0.4 bar, with the flow of permeate, depending on the cut-off membrane, being varied from 18 to 100 ml/min as follows:

3 kDa, flow=18 mL/min 5 kDa, flow=40 mL/min 10 kDa, flow=50 mL/min 30 kDa, flow=80-100 mL/min The 30 kDa cut-off membrane was found to provide a better reduction of protein contamination and filtration time, without substantial loss of GAS carbohydrate from the retentate (Table IV).

TABLE IV

| Cut-off membranes | Protein content (%) | Carbohydrate recovery (%) |
|---|---|---|
| 3 kDa | 25% | 95-100% |
| 5 kDa | 20% | 95-100% |
| 10 kDa | 8-11% | 95-100% |
| 30 kDa | 4-5% | 90% |

Q-Sepharose Chromatography

The anionic exchange chromatography step is particularly effective at reducing hyaluronic acid contamination of GAS carbohydrate as well as protein and nucleic acid content.

The step was carried out using an Akta™ system (G&E Healthcare), with the GAS carbohydrate being detected by UV absorption at 215 nm. The retentate from the ultrafiltration step was added with 100 mM NaPi buffer at pH7.2 in order to obtain a final buffer concentration of 10 mM NaPi pH7.2. This GAS carbohydrate preparation was then processed by anionic exchange chromatography using a Q Sepharose™ XL resin (G&E Healthcare) equilibrated in 10 mM NaPi buffer at pH7.2. Typically, 1 mL of resin was used for 1 mg of GAS carbohydrate. The anionic exchange chromatography may be set up to allow "flow through" of the GAS carbohydrate wherein impurities bind to the anion exchange matrix.

Figure 7:
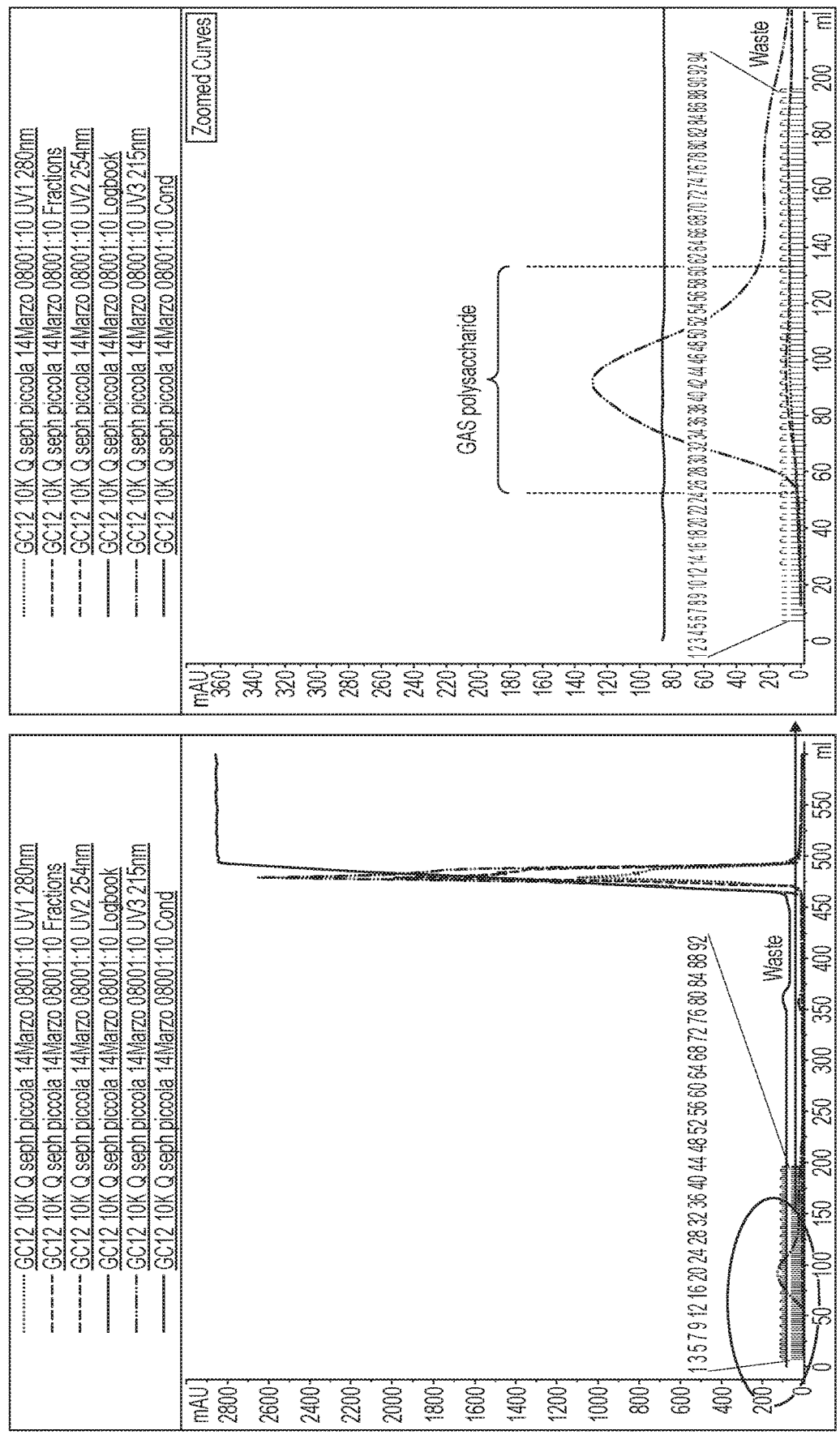
FIG. 7 shows an exemplary chromatogram for the GAS carbohydrate purified by anionic exchange chromatography on Q-Sepharose.

The GAS carbohydrate was collected in fractions of the column flow-through, appearing mainly as a single peak (FIG. 7). The fractions (except for those of the peak tail shown in FIG. 7) were pooled.

The % polysaccharide recovery, protein content and hyaluronic acid content for exemplary pooled fractions at this stage of the process are shown in Table V.

TABLE V

| Sample | Polysaccharide recovery (step yield %) | Protein content (%) | Hyaluronic acid content (%) | Nucleic acid (%) |
|---|---|---|---|---|
| 12 | 50% | 3.5% | <1% (—) | 0.4% |
| 17A | 67% | 1.3% | <1% (<0.005%) | 0.5% |
| 17B | 64% | 3.5% | <1% (—) | 0.3% |
| 19 | 44% | 2.8% | <1% (<0.005%) | 0.2% |
| 20 | 53% | 2.2% | <1% (0.005%) | 0.8% |

In an alternative method, the GAS carbohydrate preparation was processed by anionic exchange chromatography using a Q Sepharose™ FF resin (G&E Healthcare) pre-equilibrated in 100 mM NaPi buffer at pH7.2 until it reached pH 7.2 and then equilibrated in 10 mM NaPi buffer at pH7.2 to achieve a conductivity of 1.8-2.0 mS/cm. The chromatography was carried out according to Table VI:

TABLE VI

| Resin | Q Sepharose ™ Fast Flow resin (G&E Healthcare) |
|---|---|
| Polysaccharide/resin | 1 mg/ml |
| Column dimension for about 500 mg of polysaccharide | Ø = 5 cm; h = 27 cm; V = 530 ml |
| Pre-equilibration | 100 mM NaPi buffer pH 7.2 to reach pH 7.2 in the eluate |
| Equilibration | 10 mM NaPi buffer pH 7.2 to reach 1.8-2.0 mS/cm eluate conductivity |
| Product collection | 10 ml fractions pooled according to flow through peak |

10 kDa or 5 kDa Tangential Flow Filtration

The tangential flow filtration step results in concentration of the GAS carbohydrate solution. This allows the concentration of the GAS carbohydrate to be optimised for subsequent conjugation.

When the process was carried out with a 5 L fermentation, the tangential flow filtration step was carried out using a Tandem mod. 1082™ system with a Hydrosart™ 10 kDa cut-off membrane with a 200 cm$^2$ membrane area (both Sartorius). The pressure conditions were Pin=0.5 bar and Pout=0.0 bar, with the flow set at 4-5 mL/min. The filtration was continued until the desired concentration of GAS carbohydrate was reached. Diafiltration after this concentration step was avoided because it may lead to loss of GAS carbohydrate in the permeate.

Alternatively, the tangential flow filtration step was carried out using a Hydrosart™ 5 kDa cut-off membrane with a 200 cm$^2$ membrane area (Sartorius). The pressure conditions were Pin=0.7 bar and Pout=0.0 bar, with the flow set at 2 mL/min.

The final recovery of purified GAS carbohydrate after the concentration step was found to be about 300 mg from the initial 5 L fermentation.

Figure 8:
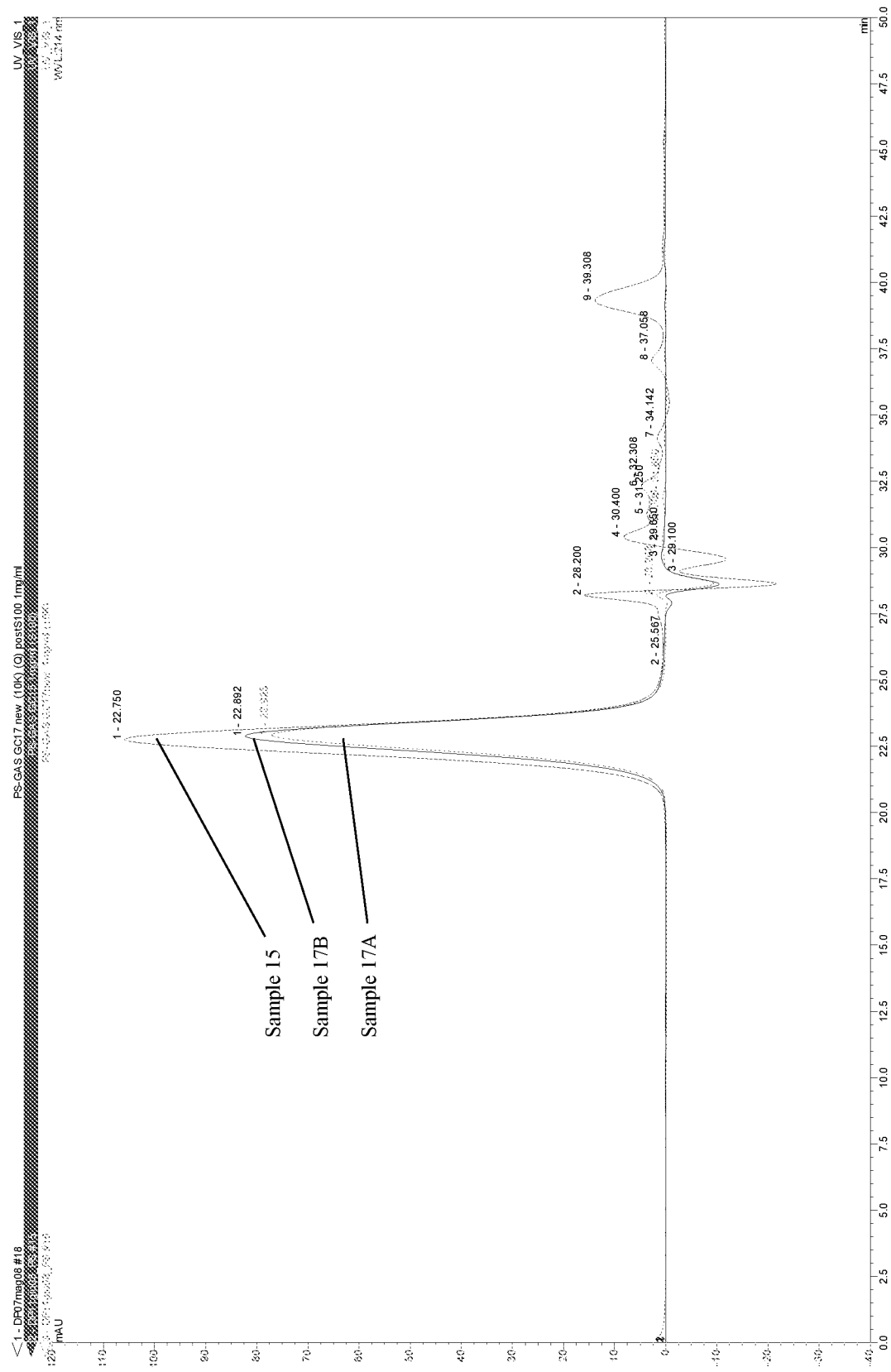
FIG. 8 shows exemplary HPLC-SE profiles for the GAS carbohydrate following concentration by tangential flow filtration.

The % polysaccharide recovery and protein, polyrhamnose, hyaluronic acid and nucleic acid content for exemplary samples at this stage of the process are shown in Table VII. HPLC-SE profiles of the purified GAS carbohydrate are shown in FIG. 8.

TABLE VII

| Sample | TFF | Polysaccharide recovery (step yield %) | Protein content (%) | Polyrhamnose content (%) | Hyaluronic acid content (%) | Nucleic acid |
|---|---|---|---|---|---|---|
| 14 | 10 kDa | 68% | 2.1% | 18% | <1% (<0.005%) | <1% (0.3%) |
| 17A | 10 kDa | 95% | 2.1% | 16% | <1% (<0.005%) | <1% (0.4%) |
| 19 | 5 kDa | 90% | 2.8% | 4% | <1% (<0.005%) | <1% (0.2%) |
| 20 | 5 kDa | 80% | 2.2% | 4.5% | <1% (<0.005%) | <1% (0.3%) |

Without wishing to be bound by theory, it is thought that the protein content (as measured by the MicroBCA assay (Pearce)) may be artificially high because of interference caused by the presence of rhamnose species in the GAS carbohydrate sample. When measured by SDS-Page gel (NuPAGE™ 7% Tris-Acetate Gel, Invitrogen) in reducing and non-reducing conditions with an excess of GAS carbohydrate sample (630 µg, implying about 12.6 µg if the protein contamination level is 2%), this high level of protein is not detected.

Figure 9:
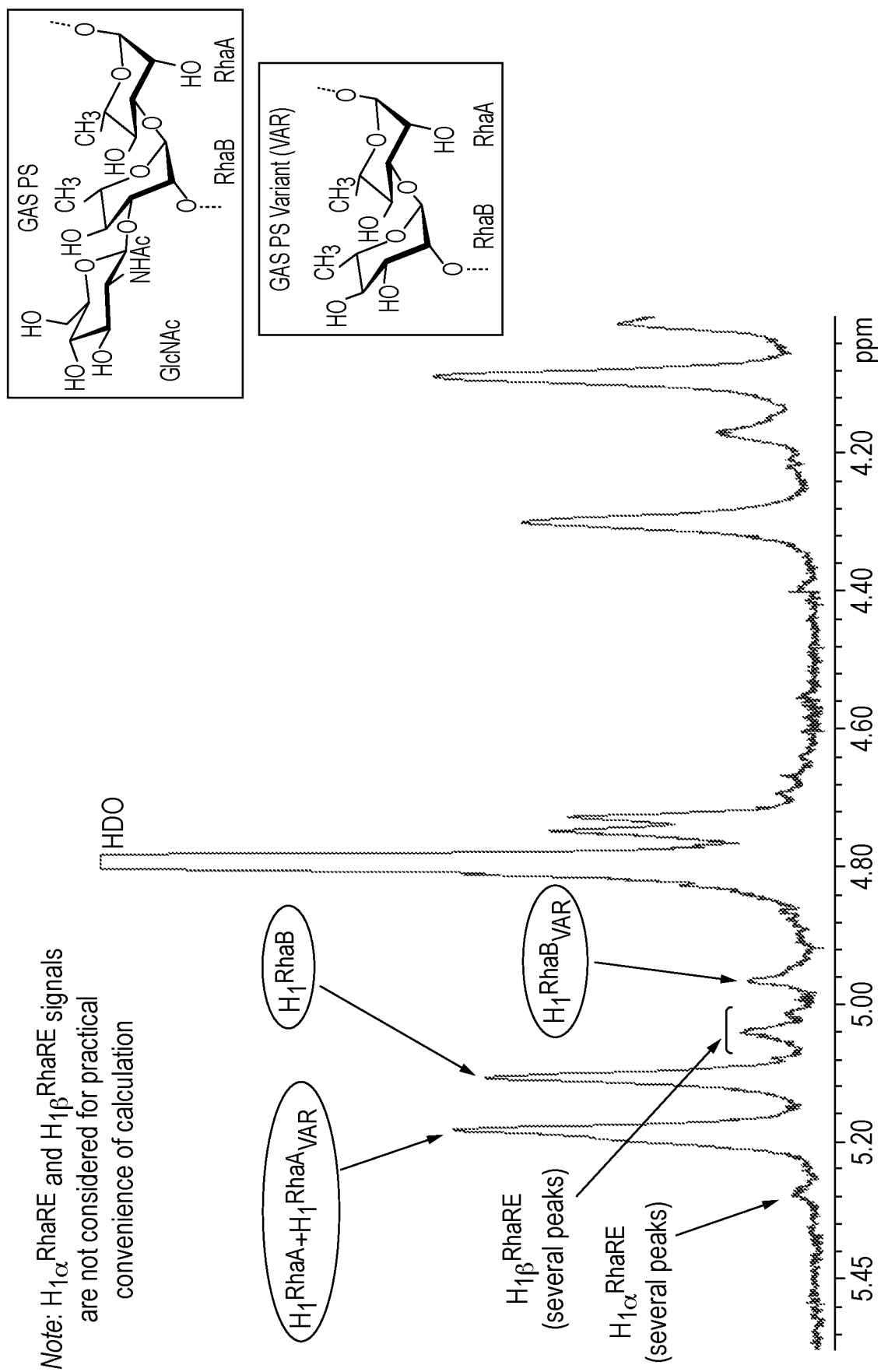
FIG. 9 shows an annotated NMR spectrum for the GAS carbohydrate after gel filtration.

Analytical Methods
Estimation of Residual Polyrhamnose Content.
Based on the NMR peak assignment (FIG. 9), the residual content of polyrhamnose was estimated by the integral ratio:

% polyrhamnose=[$H_1^{RhaB}{}_{VAR}/(H_1^{RhaA}+H_1^{RhaA}{}_{VAR})$]×100

Example 3

Comparison Between 10 kDa or 5 kDa Tangential Flow Filtration and Gel Filtration Steps In Example 1, the anionic exchange chromatography step was followed by a gel filtration step in order to further reduce contamination. In contrast, the optimised process of Example 2 involves tangential flow filtration (5 kDa or 10 kDa) instead of gel filtration at this stage of the process. The two alternatives result in roughly the same level of GAS carbohydrate recovery. However, tangential flow filtration seems to result in lower levels of polyrhamnose contamination (as measured by NMR).

Gel-Filtration Step

The chromatography was performed on an Akta™ system (G&E Healthcare), with the gel filtration being carried out with a Sephacryl S100 gel (G&E healthcare). The GAS carbohydrate preparation volume was not allowed to exceed 5% of the volume of the gel-filtration column. The mobile phase buffer was 10 mM NaPi buffer at pH7.2.

Figure 10:
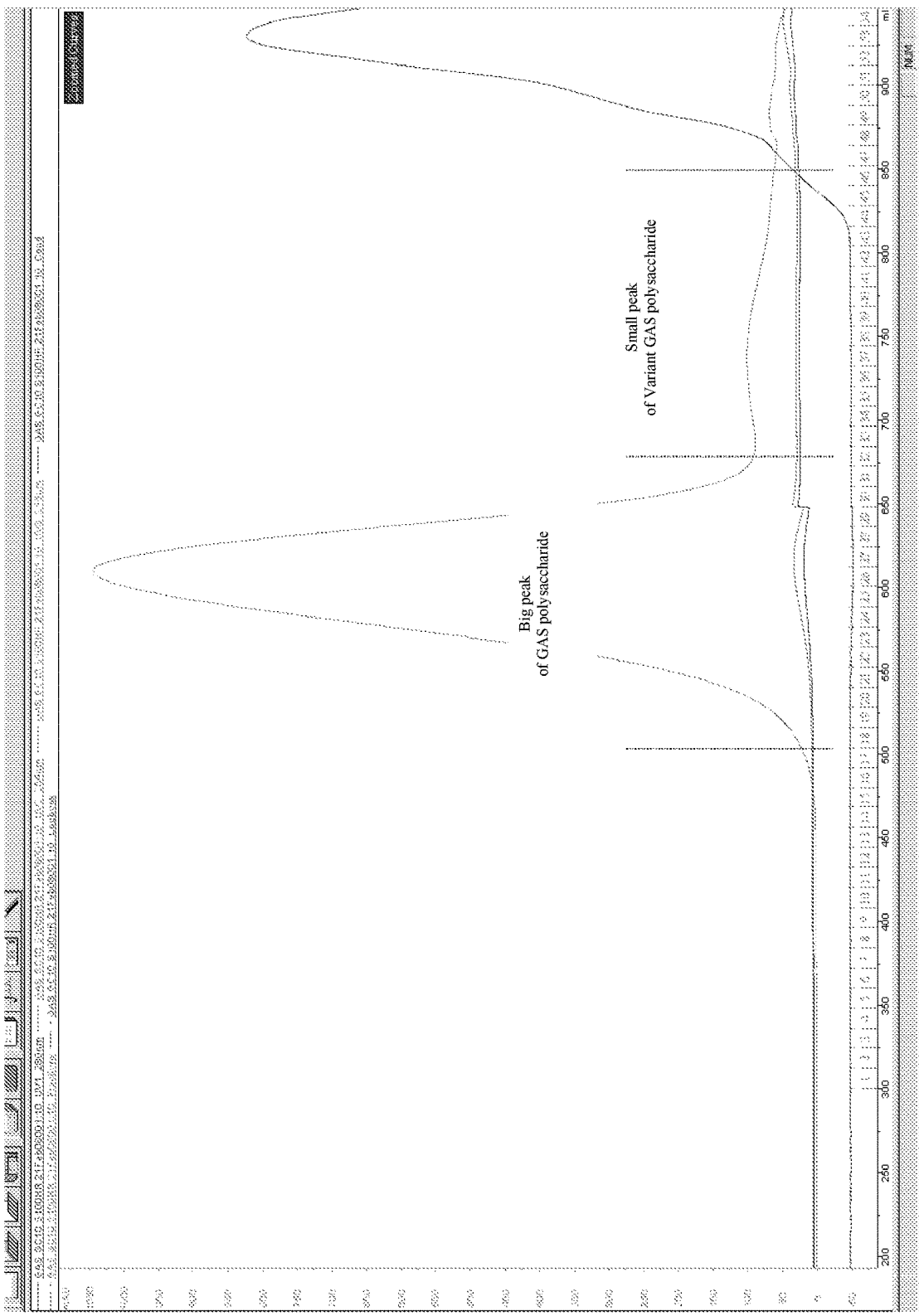
FIG. 10 shows an exemplary chromatogram for the GAS carbohydrate following gel filtration.

The polysaccharide appeared in the flow though as two peaks: a) a big peak of GAS carbohydrate and b) a small peak of polyrhamnose (FIG. 10). The amount of polyrhamnose was quite high, about 40-50% of the total polysaccharide sample.

Tangential Flow Filtration Step

In contrast, the purity of the GAS carbohydrate obtained with the optimized process is higher.

Figure 11:
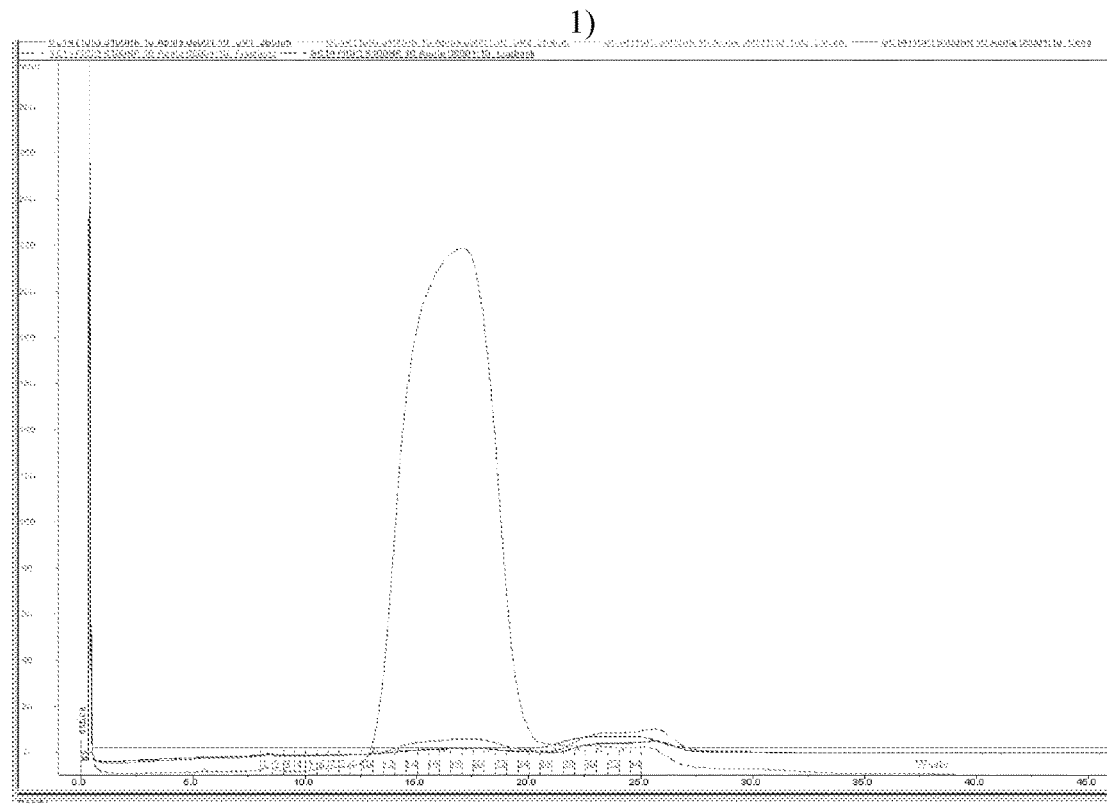
FIG. 11 shows analytical gel-filtration chromatograms performed on the GAS carbohydrate following 1) anionic chromatography step and 2) 10 kDa tangential flow filtration step.
Figure 11:
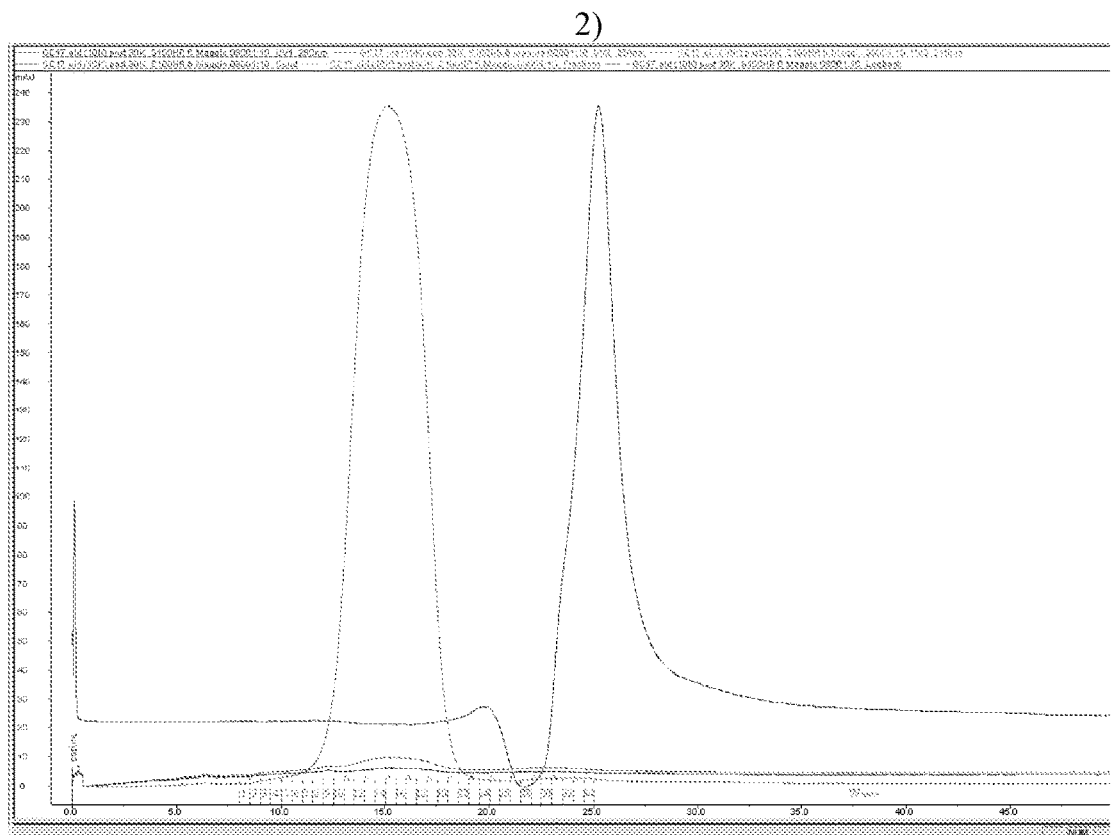

FIG. 11 shows analytical gel-filtration chromatograms of the GAS carbohydrate sample after 1) the anionic chromatography step of the optimized process and 2) the 10 kDa tangential flow filtration step of this process, which takes place after the anionic chromatography.

Figure 12:
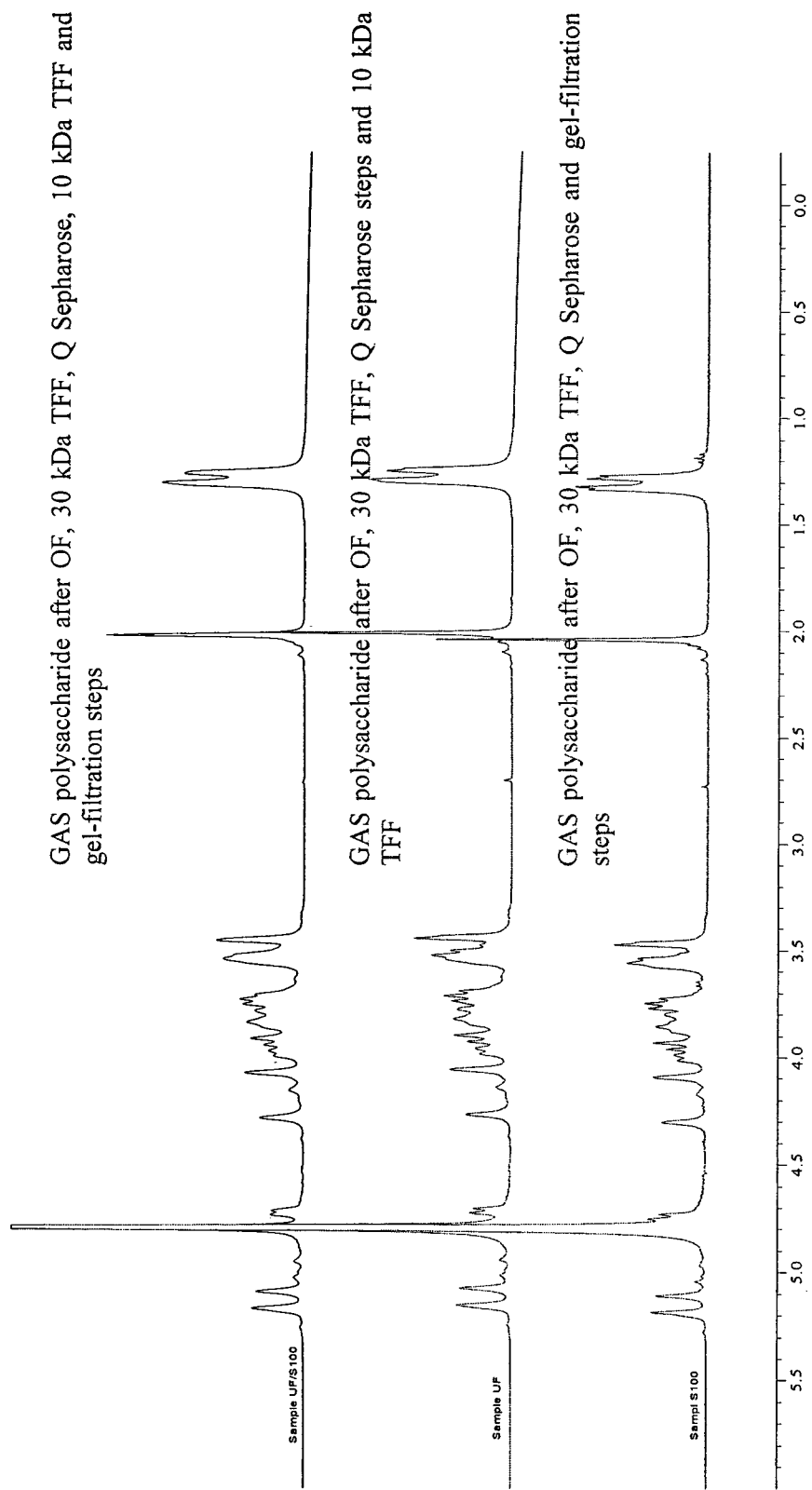
FIG. 12 shows $^1$H NMR spectra of the GAS carbohydrate following 10 kDa tangential flow filtration; 10 kDa tangential flow filtration and gel filtration; and gel filtration alone.

Material obtained from these and other gel-filtrations was compared by $^1$H NMR in order to measure the level of polyrhamnose contamination. FIG. 12 shows the spectra of samples obtained after 1) the 10 kDa tangential flow filtration step of the optimized process; 2) the 10 kDa tangential flow filtration step of the optimized process followed by a further step of gel filtration; and 3) a modified version of the optimized process in which the 10 kDa tangential flow filtration step is replaced with a step of gel filtration. The spectra are very similar, showing that the 30 kDa tangential flow filtration and anionic chromatography steps are sufficient for purifying GAS carbohydrate with a low polyrhamnose contamination (≤20%). The gel-filtration step is not required, while the concentration step performed with 10 kDa or 5 kDa tangential flow filtration is merely convenient for further processing of the GAS carbohydrate, e.g. for conjugation to a carrier molecule.

Example 4

Conjugate Preparation

Direct Reductive Amination Reaction

Figure 13:
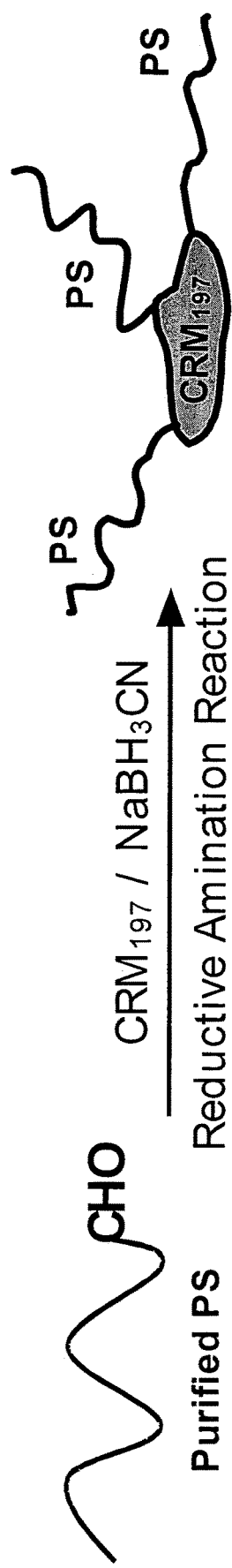
FIG. 13 illustrates a reaction scheme for obtaining a GAS carbohydrate-$CRM_{197}$ conjugate.

The purified GAS carbohydrate was conjugated to the carrier protein $CRM_{197}$ via a direct reductive amination reaction (FIG. 13). The reductive amination reaction involves an amine group on the side chain of a lysine in the carrier protein and an aldehyde group in the saccharide, specifically at the reducing end of the GAS carbohydrate polysaccharide.

Prior to conjugation, the purified GAS carbohydrate was dried in a rotavapor system. The dried GAS carbohydrate was then dissolved in NaPi 200 mM buffer at pH8.0 in order to have a final concentration of 10 mg/mL. The carrier protein, $CRM_{197}$, was added to the solution of GAS carbohydrate in NaPi 200 mM buffer at pH 8.0 and $NaBH_3CN$ (Aldrich) added. The polysaccharide:protein ratio was 4:1 (weight/weight) and the polysaccharide:$NaBCNH_3$ ratio was 2:1 (weight/weight). After reaction, the solution was 0.22 μm filtered and kept at 37° C. for 2 days.

Figure 14:
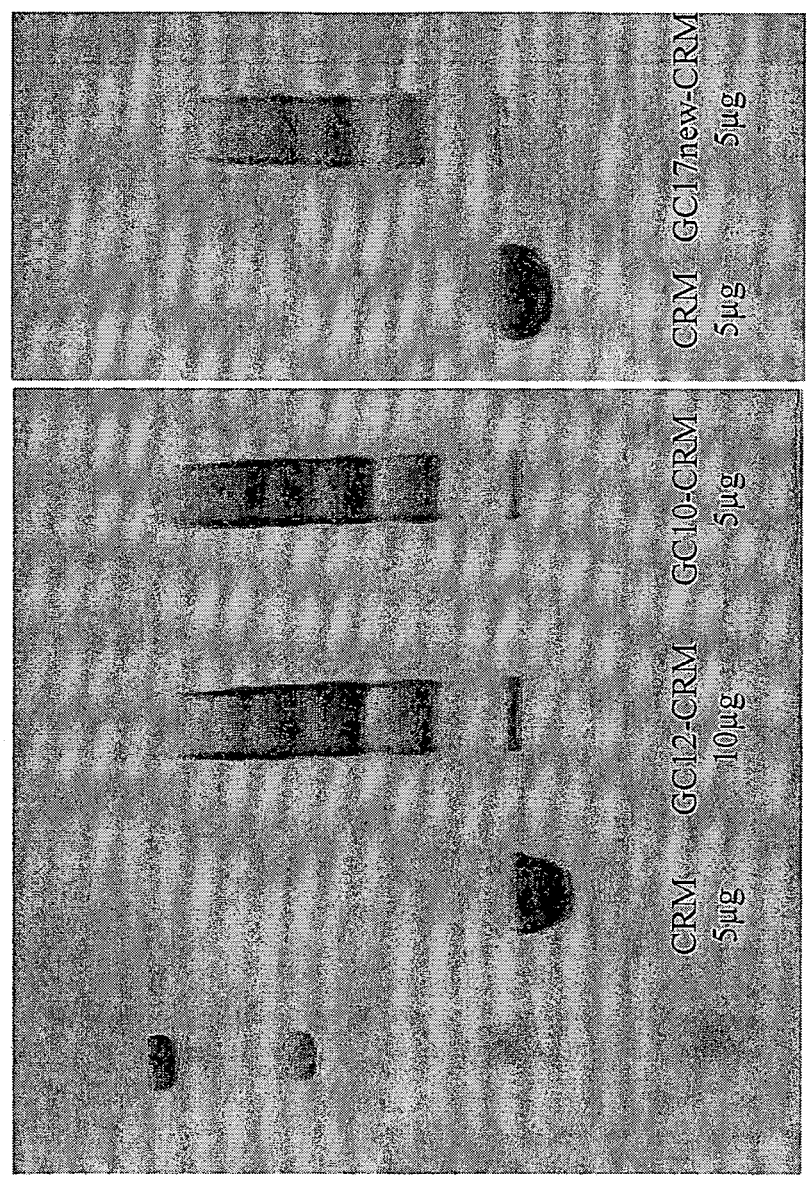
FIG. 14 shows SDS-Page gel analysis of a GAS carbohydrate-$CRM_{197}$ conjugate.

After these 2 days, SDS-Page gel analysis (NuPAGE™ 7% Tris-Acetate Gel (Invitrogen)) was performed to verify covalent conjugate formation. The results are shown in FIG. 14.

Alternative Conjugation Reaction

GAS carbohydrate may also be conjugated to a carrier molecule via a linker. The purified GAS carbohydrate was conjugated to the carrier protein $CRM_{197}$ via an adipic acid linker.

In a first step, reductive amination of the aldehyde group at the reducing end of the GAS carbohydrate polysaccharide was carried out. The purified GAS carbohydrate was dissolved in water to a final concentration of 4 mg/mL. $AcONH_4$ was added to a concentration of 300 g/L and $NaBH_3CN$ added to a 1:5 molar ratio with the $AcONH_4$. The mixture was mixed and the pH of the mixture checked to be around 7.0-7.5. The mixture was then kept at 37° C. for 60 h. Finally, the reaction mixture was purified with 10 kDa tangential flow filtration, dialyzing against NaCl 0.1M using approximately 10 volumes, and then against water using approximately 10 volumes.

In a second step, the aminated GAS carbohydrate was activated with the linker. The aminated GAS carbohydrate was first concentrated using a rotavapor system (Buchi) and then dissolved in water to a concentration of 40 μmol/mL amino groups. DMSO was added in an amount equal to 9 times the amount of water in the mixture, with $Et_3N$ being added to a 10:1 molar ratio with the amino groups. Finally, SIDEA (succinic diester of adipic acid) was added to a 12:1 molar ratio with the amino groups. The mixture was mixed at room temperature for 2 h. AcOEt (80% of the final reaction volume) and NaCl 1M (1.5% of the final reaction volume) was added drop-by-drop to the mixture, and the solution kept on ice for 1 h, during which time the activated GAS carbohydrate precipitates as a white solid. The suspension was then centrifuged at 4000 rpm (1780×g) for 15 min and the pelleted precipitate washed five times with AcOEt in an amount equal to a third of the precipitation volume (the initial volume of AcOEt used to precipitate the GAS carbohydrate). Each wash consisted of mixing for 5 min and then centrifuging at 4000 rpm for another 5 min. After washing, the precipitate was dried overnight.

In a final step, the activated GAS carbohydrate was conjugated with the $CRM_{197}$ protein. This reaction was carried out using a conjugation ratio of 20:1 between the moles of active ester group in the activated GAS carbohydrate and the moles of $CRM_{197}$. The $CRM_{197}$ was diluted to a final concentration of 20 mg/mL using NaPi 100 mM buffer at pH7.2. Subsequently, the activated GAS carbohydrate powder was gradually added to a protein solution with mild stirring. The reaction mixture was then kept under mild mixing at room temperature for 3 h.

Figure 15:
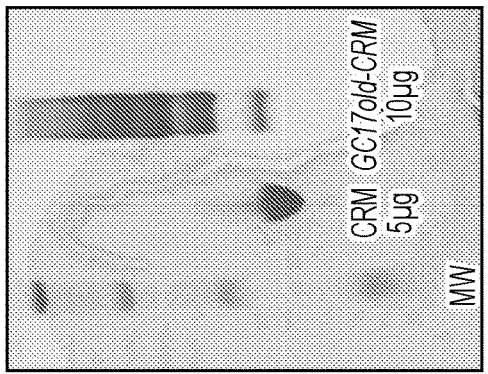
FIG. 15 shows 1) SDS-Page gel and 2) SEC-HPLC analysis of a GAS carbohydrate-$CRM_{197}$ conjugate comprising a linker.
Figure 15:
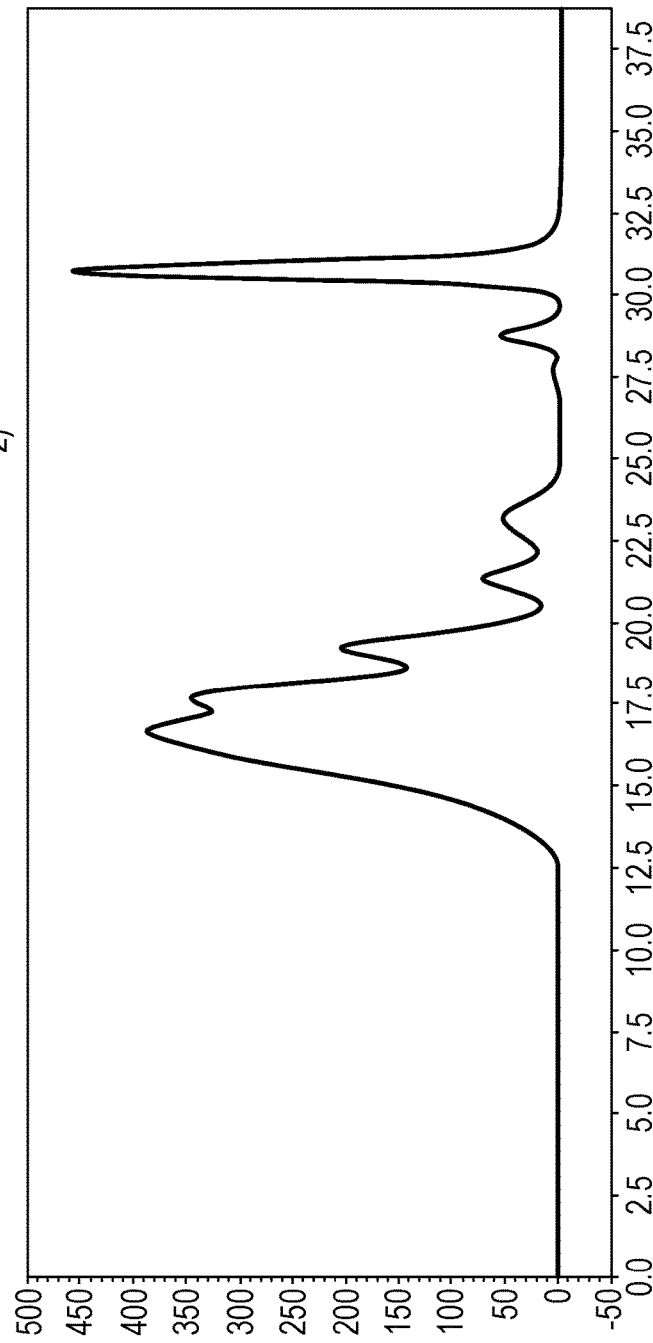

SDS-Page gel analysis (NuPAGE™ 7% Tris-Acetate Gel (Invitrogen)) was performed to verify covalent conjugate formation. SEC-HPLC analysis was also carried out. The results are shown in FIG. 15. The SDS-Page gel and SEC-HPLC analysis did not suggest any significant differences between the conjugate comprising a linker and the conjugate obtained by direct reductive amination.

Example 5

Mouse Studies

The effect of purified GAS carbohydrate conjugated to $CRM_{197}$ via the direct reductive amination reaction was tested in an intraperitoneal GAS challenge assay. Mice were immunised with conjugate (at a does of 10 μg saccharide) by intraperitoneal administration with an alum adjuvant. When challenged with the M1 strain of *Streptococcus pyogenes*, 51% of mice survived as compared to 16% of non-immunised controls. In another study, mice were challenged with either the M1 or M23 strains. In this study, 56% of the immunised mice challenged with the M1 strain survived compared to 20% of non-immunised controls, while 41% of mice challenged with the M23 strain survived compared to 11% in controls. Accordingly, GAS carbohydrate purified by the method of the invention provides protective immunity.

It will be understood that the invention has been described by way of example only and modifications may be made whilst remaining within the scope and spirit of the invention.

REFERENCES

[1] Bisno et al. (2005) *Clin Infect Dis.* 41(8):1150-6.
[2] Cohen-Poradosu and Kasper (2007) *Clin Infect Dis.* 45(7):863-5.
[3] World Health Organization. Dept. of Child and Adolescent Health and Development (2005) Group A streptococcal vaccine development: current status and issues of relevance to less developed countries (WHO/FCH/CAH/05.09; WHO/IVB/05.14)
[4] McCarty (1958) *J Exp Med.* 108(3):311-23.
[5] Dubois et al. (1956) *Anal. Chem.* 28:350-356.
[6] U.S. Pat. No. 5,866,135.
[7] Pancholi and Fischetti (1988) *J Bacteria* 170(6):2618-24.
[8] Sabharwal et al. (2006) *J Infect Dis.* 193(1):129-35.
[9] Sabharwal et al. (2006) *International Congress Series* 1289:329-331.
[10] Michon et al. (2005) *Infect Immun.* 73(10):6383-9.
[11] Fillit et al. (1986) *J Exp Med.* 164(3):762-76.
[12] Cunningham in *Gram-Positive Pathogens*, Eds. Fischetti et al., ASM Press, Washington D.C. (2006) ISBN: 9781555813437.
[13] Martins et al. (2008) *Int Immunol.* 20(3):445-52.
[14] Kreis et al. (1995) *Int J Biol Macromol.* 17(3-4):117-30.
[15] Hoog et al. (2002) *Carbohydr Res.* 337(21-23):2023-36
[16] www.polymer.de
[17] Park and Johnson (1949) *J. Biol. Chem.* 282, 149-151.
[18] Wessels et al. (1989) *Infect Immun* 57:1089-94.
[19] Ramsay et al. (2001) *Lancet* 357(9251):195-196.
[20] Lindberg (1999) *Vaccine* 17 Suppl 2:S28-36.
[21] Buttery & Moxon (2000) *J R Coll Physicians Lond* 34:163-68.
[22] Ahmad & Chapnick (1999) *Infect Dis Clin North Am* 13:113-33, vii.
[23] Goldblatt (1998) *J. Med. Microbiol.* 47:563-7.
[24] European patent 0477508.
[25] U.S. Pat. No. 5,306,492.
[26] WO98/42721.
[27] Dick et al. in *Conjugate Vaccines* (eds. Cruse et al.) Karger, Basel, 1989, 10:48-114.
[28] Hermanson *Bioconjugae Techniques*, Academic Press, San Diego (1996) ISBN: 0123423368.
[29] Jennings and Lugowski (1981) *J Immunol.* 127(3): 1011-8.
[30] U.S. Pat. No. 4,882,317
[31] U.S. Pat. No. 4,695,624
[32] EP-B-0 477 508
[33] *Mol. Immunol.*, 1985, 22, 907-919
[34] EP-A-0208375
[35] Bethell G. S. et al., *J. Biol. Chem.*, 1979, 254, 2572-4
[36] Hearn M. T. W., *J. Chromatogr.*, 1981, 218, 509-18
[37] WO00/10599
[38] Gever et al., Med. Microbiol. Immunol, 165: 171-288 (1979).
[39] U.S. Pat. No. 4,057,685.
[40] U.S. Pat. Nos. 4,673,574; 4,761,283; 4,808,700.
[41] U.S. Pat. No. 4,459,286.
[42] U.S. Pat. No. 5,204,098
[43] U.S. Pat. No. 4,965,338
[44] U.S. Pat. No. 4,663,160.
[45] WO2007/000343.
[46] WO 2006/082530.
[47] *Research Disclosure*, 453077 (January 2002)
[48] EP-A-0372501.
[49] EP-A-0378881.
[50] EP-A-0427347.
[51] WO93/17712
[52] WO94/03208.
[53] WO98/58668.
[54] EP-A-0471177.
[55] WO91/01146
[56] Falugi et al. (2001) *Eur J Immunol* 31:3816-3824.
[57] Baraldo et al. (2004) *Infect Immun* 72(8):4884-7.
[58] EP-A-0594610.
[59] Ruan et al. (1990) *J Immunol* 145:3379-3384.
[60] WO00/56360.
[61] Kuo et al. (1995) *Infect Immun* 63:2706-13.
[62] Michon et al. (1998) *Vaccine.* 16:1732-41.
[63] WO02/091998.
[64] WO01/72337
[65] WO00/61761.
[66] WO00/33882
[67] WO02/34771.
[68] WO99/42130.
[69] WO2004/011027.
[70] WO96/40242.
[71] Lei et al. (2000) *Dev Biol (Basel)* 103:259-264.
[72] WO00/38711; U.S. Pat. No. 6,146,902.
[73] WO99/24578.
[74] WO99/36544.
[75] WO99/57280.
[76] WO00/22430.
[77] Tettelin et al. (2000) *Science* 287:1809-1815.
[78] WO96/29412.
[79] Pizza et al. (2000) *Science* 287:1816-1820.
[80] WO01/52885.
[81] Bjune et al. (1991) *Lancet* 338(8775):1093-1096.
[82] Fukasawa et al. (1999) *Vaccine* 17:2951-2958.
[83] Rosenqvist et al. (1998) *Dev. Biol. Stand.* 92:323-333.
[84] Costantino et al. (1992) *Vaccine* 10:691-698.
[85] WO03/007985.
[86] Watson (2000) *Pediatr Infect Dis J* 19:331-332.
[87] Rubin (2000) *Pediatr Clin North Am* 47:269-285, v.

[88] Jedrzejas (2001) *Microbiol Mol Biol Rev* 65:187-207.
[89] Bell (2000) *Pediatr Infect Dis J* 19:1187-1188.
[90] Iwarson (1995) *APMIS* 103:321-326.
[91] Gerlich et al. (1990) *Vaccine* 8 Suppl:S63-68 & 79-80.
[92] Hsu et al. (1999) *Clin Liver Dis* 3:901-915.
[93] Gustafsson et al. (1996) *N. Engl. J. Med.* 334:349-355.
[94] Rappuoli et al. (1991) *TIBTECH* 9:232-238.
[95] Vaccines (2004) eds. Plotkin & Orenstein. ISBN 0-7216-9688-0.
[96] WO02/02606.
[97] Kalman et al. (1999) *Nature Genetics* 21:385-389.
[98] Read et al. (2000) *Nucleic Acids Res* 28:1397-406.
[99] Shirai et al. (2000) *J. Infect. Dis.* 181(Suppl 3):S524-S527.
[100] WO99/27105.
[101] WO00/27994.
[102] WO00/37494.
[103] WO99/28475.
[104] Ross et al. (2001) *Vaccine* 19:4135-4142.
[105] Sutter et al. (2000) *Pediatr Clin North Am* 47:287-308.
[106] Zimmerman & Spann (1999) *Am Fam Physician* 59:113-118, 125-126.
[107] Dreesen (1997) *Vaccine* 15 Suppl:S2-6.
[108] *MMWR Morb Mortal Wkly Rep* 1998 Jan. 16; 47(1): 12, 19.
[109] McMichael (2000) *Vaccine* 19 Suppl 1:S101-107.
[110] WO03/093306.
[111] WO2004/018646.
[112] WO2004/041157.
[113] Robinson & Torres (1997) *Seminars in Immunology* 9:271-283.
[114] Donnelly et al. (1997) *Annu Rev Immunol* 15:617-648.
[115] Scott-Taylor & Dalgleish (2000) *Expert Opin Investig Drugs* 9:471-480.
[116] Apostolopoulos & Plebanski (2000) *Curr Opin Mol Ther* 2:441-447.
[117] Ilan (1999) *Curr Opin Mol Ther* 1:116-120.
[118] Dubensky et al. (2000) *Mol Med* 6:723-732.
[119] Robinson & Pertmer (2000) *Adv Virus Res* 55:1-74.
[120] Donnelly et al. (2000) *Am J Respir Crit. Care Med* 162(4 Pt 2):S190-193.
[121] Davis (1999) *Mt. Sinai J. Med.* 66:84-90.
[122] Gennaro (2000) *Remington: The Science and Practice of Pharmacy.* 20th edition, ISBN: 0683306472.
[123] Almeida & Alpar (1996) *J. Drug Targeting* 3:455-467.

The invention claimed is:

1. A process for purifying group A *streptococcus* (GAS) carbohydrate, comprising:
 a first step of filtration or ultrafiltration of an aqueous suspension of GAS carbohydrate, polyrhamnose, and hyaluronic acid, wherein said aqueous suspension was prepared by reductive acid treatment of GAS bacteria such that the GAS carbohydrate, polyrhamnose and the hyaluronic acid were released from the GAS bacteria;
 a second step of anionic exchange chromatography on a mixture comprising the GAS carbohydrate, polyrhamnose and the hyaluronic acid from the first step, wherein the anionic exchange chromatography is performed under conditions that allow flow through of the GAS carbohydrate and less than 1% by weight of the hyaluronic acid, and
 a third step, which comprises tangential flow filtration using a 5 or 10 kDa cut-off membrane of a mixture comprising the GAS carbohydrate from the second step,
 wherein the process yields a purified GAS carbohydrate comprising a level of hyaluronic acid contamination that is: a) less than 80 ng/ml; or b) less than 1% by weight of the hyaluronic acid relative to the weight of the GAS carbohydrate; and a polyrhamnose impurity of less than 20% by weight of the polyrhamnose relative to the weight of the GAS carbohydrate.

2. The process of claim 1, wherein the purified GAS carbohydrate has a molecular weight of about 10 kDa.

3. The process of claim 1 or claim 2, wherein the GAS carbohydrate is partially or fully de-N-acetylated.

4. The process of claim 1, wherein the first step is the filtration and the filtration is by orthogonal filtration using a 0.65 μm filter.

5. The process of claim 1, wherein the first step is the ultrafiltration and the ultrafiltration is by tangential flow filtration using a 30 kDa cut-off membrane.

6. The process of claim 1, wherein the anionic exchange chromatography step is carried out using a Q-resin as anionic exchange matrix.

7. The process of claim 1, wherein the anionic exchange chromatography step is carried out using 1 mL of anionic exchange matrix resin for every 1 mg of GAS carbohydrate.

8. The process of claim 1, wherein a mobile phase buffer for the anionic exchange chromatography comprises alcohol.

9. The process of claim 8, wherein the final alcohol concentration in the mobile phase buffer is between 15% and 25%.

10. The process of claim 8 or claim 9, wherein the alcohol is ethanol.

11. The process of claim 1, wherein the process comprises one or more gel filtration step(s) after the anionic exchange chromatography step.

12. The process of claim 11, wherein the gel filtration step(s) are carried out using a dextran gel as gel filtration matrix.

13. The process of claim 11 or claim 12, wherein the gel filtration step(s) are carried out using 1 mL of gel filtration matrix for every 0.2 mg of GAS carbohydrate.

14. The process of claim 11, wherein the gel filtration step(s) are performed using a mobile phase buffer, which is the same as a mobile phase buffer used in the anionic exchange chromatography step.

15. The process of claim 11, wherein the gel filtration step(s) are performed using a mobile phase buffer comprising alcohol at a concentration between 15% and 25%.

16. The process of claim 1, wherein the process comprises one or more steps of concentrating the GAS carbohydrate after the anionic exchange chromatography step.

17. The process of claim 1, wherein the process includes a further step of conjugating the purified GAS carbohydrate to a carrier molecule.

18. The process of claim 1, further comprising formulating the purified GAS carbohydrate into a pharmaceutical composition.

19. The process of claim 1, wherein the anionic exchange chromatography step is carried out using a DEAE resin as anionic exchange matrix.

20. The process of claim 1, wherein the third step comprises tangential flow filtration using the 5 kDa cut-off membrane.

21. The process of claim 1, wherein the polyrhamnose impurity is less than 4.5% by the weight of the polyrhamnose relative to the weight of the GAS carbohydrate.

* * * * *

UNITED STATES PATENT AND TRADEMARK OFFICE
CERTIFICATE OF CORRECTION

| | |
|---|---|
| PATENT NO. | : 11,065,323 B2 |
| APPLICATION NO. | : 13/126146 |
| DATED | : July 20, 2021 |
| INVENTOR(S) | : Costantino et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 92 days.

Signed and Sealed this
Thirtieth Day of August, 2022

Katherine Kelly Vidal
*Director of the United States Patent and Trademark Office*